(12) United States Patent
Golden et al.

(10) Patent No.: US 10,433,890 B2
(45) Date of Patent: Oct. 8, 2019

(54) JOINT REPAIR SYSTEM

(71) Applicant: Coracoid Solutions, LLC, Park City, UT (US)

(72) Inventors: Steven S. Golden, Menlo Park, CA (US); Robert Fernandez, Campbell, CA (US); Nathaniel Cohen, Los Gatos, CA (US); Phil Davidson, Park City, UT (US); Treg Brown, Carbondale, IL (US); Mark Dorighi, San Jose, CA (US); Heber Saravia, San Francisco, CA (US)

(73) Assignee: CORACOID SOLUTIONS, LLC, Park City, UT (US)

( * ) Notice: Subject to any disclaimer, the term of this patent is extended or adjusted under 35 U.S.C. 154(b) by 0 days.

(21) Appl. No.: 15/714,724

(22) Filed: Sep. 25, 2017

(65) Prior Publication Data
US 2018/0014865 A1 Jan. 18, 2018

Related U.S. Application Data

(63) Continuation of application No. PCT/US2016/024246, filed on Mar. 25, 2016.
(Continued)

(51) Int. Cl.
*A61B 17/80* (2006.01)
*A61B 17/84* (2006.01)
(Continued)

(52) U.S. Cl.
CPC ........ *A61B 17/842* (2013.01); *A61B 17/0469* (2013.01); *A61B 17/0482* (2013.01);
(Continued)

(58) Field of Classification Search
None
See application file for complete search history.

(56) References Cited

U.S. PATENT DOCUMENTS

| 94,728 A | 1/1910 | Sourek |
| 1,301,102 A | 4/1919 | Cary |

(Continued)

FOREIGN PATENT DOCUMENTS

| AU | 2016238296 | 9/2018 |
| DE | 3538645 | 5/1987 |

(Continued)

OTHER PUBLICATIONS

PCT/US2016/024246, "International Search Report and Written Opinion", dated Jun. 24, 2016, 10 pages.
(Continued)

*Primary Examiner* — Sameh R Boles
(74) *Attorney, Agent, or Firm* — Kilpatrick Townsend & Stockton LLP

(57) ABSTRACT

A joint stabilization (reduction) system and associated methods and tools for placement of the system in an open or minimally invasive technique. The joint stabilization system includes a flexible prosthetic band for stabilizing the bones in proper position and a connector mechanism for joining the two ends of the prosthetic band around the bones. One end of the prosthetic band can be permanently attached to the connector.

17 Claims, 29 Drawing Sheets

Related U.S. Application Data

(60) Provisional application No. 62/138,342, filed on Mar. 25, 2015.

(51) Int. Cl.

| | | |
|---|---|---|
| *A61F 2/08* | (2006.01) | |
| *A61B 17/12* | (2006.01) | |
| *A61B 17/22* | (2006.01) | |
| *A61F 5/00* | (2006.01) | |
| *A61B 17/34* | (2006.01) | |
| *A61B 17/04* | (2006.01) | |
| *A61B 17/82* | (2006.01) | |
| *A61B 17/88* | (2006.01) | |
| *A61B 17/00* | (2006.01) | |
| *A61B 17/56* | (2006.01) | |
| *A61B 17/06* | (2006.01) | |

(52) U.S. Cl.
 CPC ............. *A61B 17/12* (2013.01); *A61B 17/22* (2013.01); *A61B 17/3468* (2013.01); *A61B 17/82* (2013.01); *A61B 17/8861* (2013.01); *A61F 2/08* (2013.01); *A61F 2/0811* (2013.01); *A61F 5/00* (2013.01); *A61B 17/0483* (2013.01); *A61B 17/0485* (2013.01); *A61B 17/8061* (2013.01); *A61B 2017/00331* (2013.01); *A61B 2017/00358* (2013.01); *A61B 2017/00858* (2013.01); *A61B 2017/00862* (2013.01); *A61B 2017/00867* (2013.01); *A61B 2017/00955* (2013.01); *A61B 2017/0474* (2013.01); *A61B 2017/06042* (2013.01); *A61B 2017/06095* (2013.01); *A61B 2017/564* (2013.01); *A61F 2002/0858* (2013.01)

(56) References Cited

U.S. PATENT DOCUMENTS

| | | |
|---|---|---|
| 1,333,260 A | 3/1920 | Kerngood |
| 1,348,485 A | 8/1920 | Dietze |
| 1,436,448 A | 11/1922 | Kimball et al. |
| 1,652,813 A | 12/1927 | Cary |
| 1,853,889 A | 4/1932 | Alterson |
| 1,934,951 A | 11/1933 | Schaefer |
| 3,570,497 A | 3/1971 | Lemole |
| 3,678,542 A | 7/1972 | Prete, Jr. |
| 4,119,091 A | 10/1978 | Partridge |
| 4,730,615 A | 3/1988 | Sutherland et al. |
| 5,161,351 A | 11/1992 | Woodruff |
| 5,330,489 A | 7/1994 | Green et al. |
| 5,336,231 A | 8/1994 | Adair |
| 5,355,913 A | 10/1994 | Green et al. |
| 5,356,412 A | 10/1994 | Golds et al. |
| 5,356,417 A | 10/1994 | Golds et al. |
| 5,486,183 A | 1/1996 | Middleman et al. |
| 5,487,746 A | 1/1996 | Yu et al. |
| 5,501,688 A | 3/1996 | Whiteside |
| 5,601,572 A | 2/1997 | Middleman et al. |
| 5,725,582 A | 3/1998 | Bevan et al. |
| 5,741,276 A | 4/1998 | Poloyko et al. |
| 5,766,218 A | 6/1998 | Arnott et al. |
| 5,810,825 A | 9/1998 | Huebner |
| 5,810,832 A | 9/1998 | Blaisingame et al. |
| 5,851,209 A | 12/1998 | Kummer et al. |
| 5,919,199 A | 7/1999 | Mers Kelly et al. |
| 5,972,006 A | 10/1999 | Sciaino |
| 6,050,998 A | 4/2000 | Fletcher |
| 6,517,578 B2 | 2/2003 | Hein |
| 7,444,720 B2 | 11/2008 | Huang |
| 7,658,751 B2 | 2/2010 | Stone et al. |
| 8,162,997 B2 | 4/2012 | Struhl |
| 8,257,356 B2 | 9/2012 | Bleich et al. |
| 8,313,513 B2 | 11/2012 | Beger et al. |
| 8,460,295 B2 | 6/2013 | McClellan et al. |
| 8,486,114 B2 | 7/2013 | Gillard et al. |
| 8,512,379 B2 | 8/2013 | Heino et al. |
| 8,579,901 B1 | 11/2013 | Foerster et al. |
| 8,974,367 B2 | 3/2015 | Goddard |
| 2003/0208210 A1 | 11/2003 | Dreyfuss et al. |
| 2004/0097975 A1 | 5/2004 | Rose et al. |
| 2005/0171547 A1* | 8/2005 | Aram ................. A61B 17/82 |
| | | 606/74 |
| 2006/0106391 A1 | 5/2006 | Huebner |
| 2006/0122458 A1* | 6/2006 | Bleich ............ A61B 17/1659 |
| | | 600/101 |
| 2007/0198087 A1 | 8/2007 | Coleman et al. |
| 2007/0270861 A1 | 11/2007 | Leisinger |
| 2007/0270878 A1 | 11/2007 | Leisinger |
| 2007/0276437 A1 | 11/2007 | Call et al. |
| 2010/0125297 A1 | 5/2010 | Struhl |
| 2010/0185161 A1 | 7/2010 | Pellegrino et al. |
| 2010/0234896 A1 | 9/2010 | Lorenz et al. |
| 2011/0004260 A1 | 1/2011 | Sherman et al. |
| 2011/0313435 A1 | 12/2011 | Aldridge et al. |
| 2012/0123474 A1 | 5/2012 | Zajac et al. |
| 2012/0143206 A1 | 6/2012 | Wallace et al. |
| 2013/0261625 A1 | 10/2013 | Koch |
| 2014/0018828 A1 | 1/2014 | Foerster et al. |
| 2014/0214054 A1 | 7/2014 | Foerster et al. |
| 2014/0249530 A1 | 9/2014 | Babikian et al. |
| 2014/0257302 A1 | 9/2014 | Nino et al. |
| 2015/0088165 A1 | 3/2015 | Murray et al. |
| 2015/0148852 A1 | 5/2015 | Zhang et al. |
| 2015/0196294 A1 | 7/2015 | Murillo et al. |
| 2018/0116701 A1 | 5/2018 | Golden et al. |

FOREIGN PATENT DOCUMENTS

| | | |
|---|---|---|
| DE | 4024334 | 2/1992 |
| DE | 202014101493 | 5/2014 |
| EP | 876798 | 11/1998 |
| FR | 2977787 | 1/2013 |
| JP | 2003265491 | 9/2003 |
| JP | 2006288864 | 10/2006 |
| WO | 2006136938 | 12/2006 |
| WO | 2011031854 | 3/2011 |
| WO | 2012116266 | 8/2012 |
| WO | 2013007911 | 1/2013 |
| WO | 2014128551 | 8/2014 |
| WO | 2014144479 | 9/2014 |

OTHER PUBLICATIONS

AU2016238296, "First Examination Report", dated Dec. 13, 2017, 10 pages.
CA2,980,742, "Office Action", dated Nov. 10, 2017, 4 pages.
Cook et al., "Clavicular Bone Tunnel Malposition Leads to Early Failures in Coracoclavicular Ligament Reconstructions.", The American Journal of Sports Medicine, vol. 41, No. 1, 2013, pp. 142-148.
KR10-2017-7030652, "Office Action", dated Dec. 6, 2017, 14 pages.
AU2016238296, "Notice of Acceptance", dated Jun. 4, 2018, 3 pages.
CA2,980,742, "Office Action", dated Jul. 6, 2018, 4 pages.
EP16769779.6, "Partial Supplementary European Search Report", dated Jun. 28, 2018, 11 pages.
KR10-2017-7030652, "Office Action", dated May 31, 2018, 7 pages.
U.S. Appl. No. 15/561,467, "Non-Final Office Action", dated Nov. 29, 2018, 7 pages.
EP16769779.6, "Extended European Search Report", dated Oct. 8, 2018, 10 pages.
JP2018-502046, "Office Action", dated Sep. 18, 2018, 17 pages.
KR10-2017-7030652, "Office Action", dated Oct. 1, 2018, 6 pages.

* cited by examiner

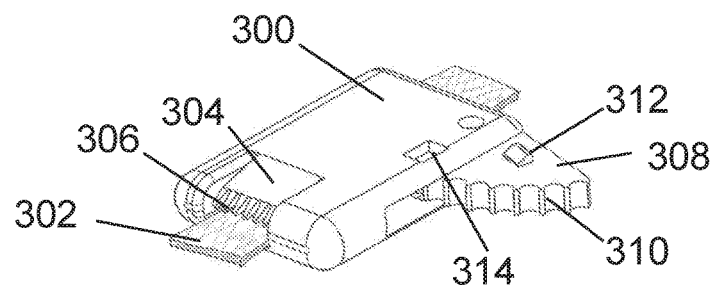
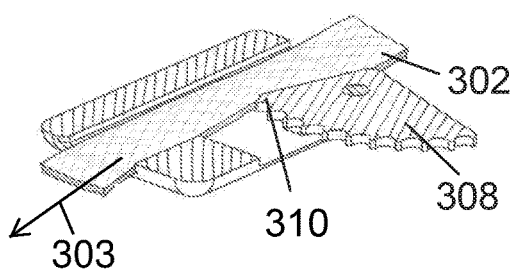
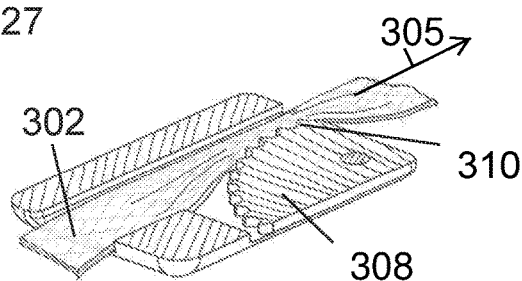
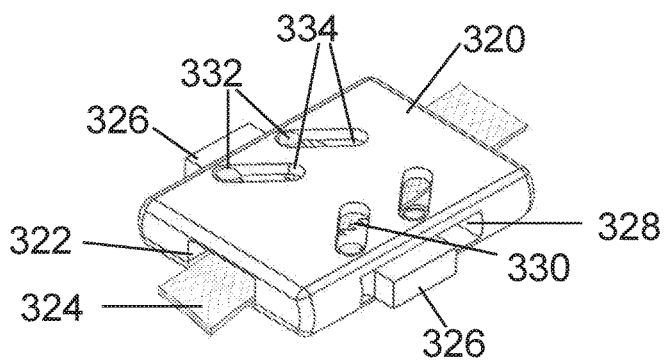
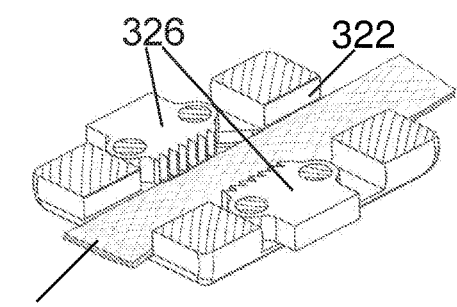
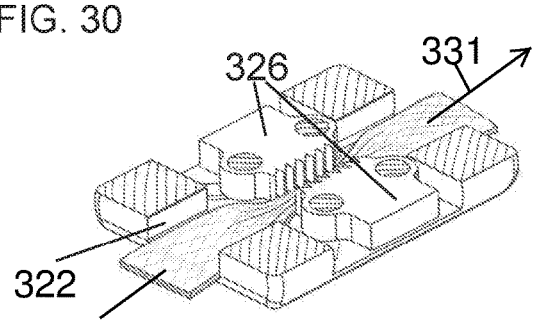

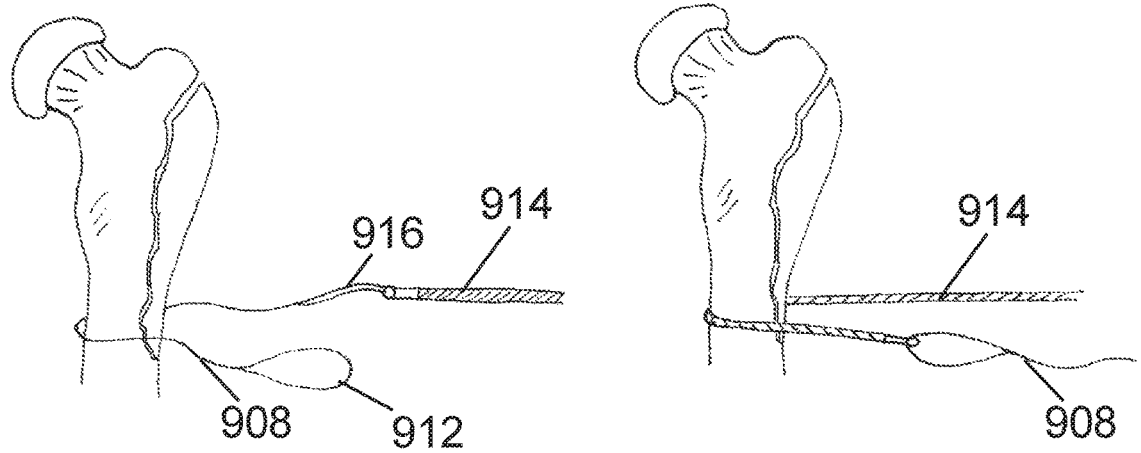
FIG. 84
FIG. 85
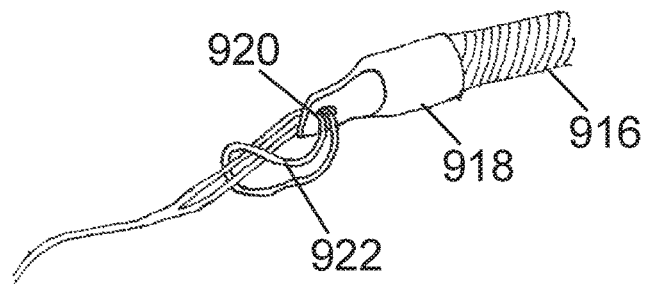
FIG. 86
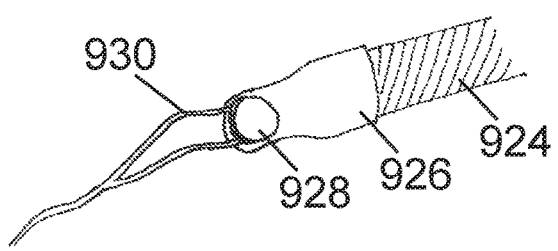
FIG. 87

JOINT REPAIR SYSTEM

CROSS REFERENCE TO RELATED APPLICATION

This application is a continuation of International Application No. PCT/US2016/024246, filed Mar. 25, 2016, which application claims the benefit of U.S. Provisional Application No. 62/138,342, filed Mar. 25, 2015, the entire contents of which are hereby incorporated by reference in their entirety for all purposes.

BACKGROUND

Joint dislocations in the human body are an increasingly common occurrence. Many of these dislocations involve varying degrees of associated ligament damage. Often, in minor injuries, the ligaments are able to heal with rest and external immobilization. However, more severe or chronic injuries to the joint require surgical intervention and internal stabilization or "casting" of the bone forming the joint to allow for proper healing. Common joint dislocations of this type include the acromioclavicular joint of the shoulder, which involves: (1) the acromioclavicular (AC) ligaments that join the clavicle and the acromium of the scapula; and (2) the coracoclavicular (CC) ligaments that join the coracoid bone to the clavicle. Other syndesmotic joints such as the distal tibiofibular joints are often similarly dislocated with associated ligament damage. In the case of the AC joint injury, commonly known as "separated shoulder", AC ligaments and the CC ligaments are injured, causing upward displacement of the clavicle bone relative to both the acromium and coracoid bones. Surgical stabilization of such an injured joint involves the reduction of the clavicle relative to these bones, typically via some sort of mechanism designed to pull the clavicle down into proper alignment and hold it there while healing occurs.

Surgical techniques have been developed to accomplish this stabilization and numerous mechanisms have been devised. For an open surgical approach, sutures or other band-like devices are placed around the coracoid and attached over the clavicle. Often a tendon graft is utilized in this manner to provide a biological proxy to the injured ligaments. However, there is an ever-increasing demand for more minimally invasive surgical techniques. Minimally invasive or arthroscopic techniques have been developed and mechanisms devised (e.g., Guerra US 2010/0125297 and Struhl U.S. Pat. No. 8,162,997) to address the need for minimally invasive approaches. Typically, these mechanisms and techniques involve drilling bone tunnels through the clavicle and subsequently through the coracoid bone, then inserting a suture-based tether between the two bones held by metal buttons on the opposing sides of the bones. These procedures can be technically demanding and are associated with high failure rates (Cook et al., Am J. Sports MEd 2013 41: 142). The lower morbidity seen in percutaneous, endoscopic and arthroscopic surgery makes these techniques very appealing to both patients and physicians. Often, the bone tunnel formation has been associated with bone fractures as well.

One of the primary issues with performing these surgical procedures in a minimally invasive fashion is that of access to the deep-lying bones that are surrounded by soft tissue. Gaining access to the opposing side of the bone in order to place a prosthesis or passing suture is very technically demanding and often not possible. Others, mentioned previously, have attempted to solve this issue by drilling a hole through the most surface-adjacent bone and continuing the drill hole through the deeper lying bone. A suture construct with toggling metal buttons is then passed through the holes in both bones, which tethers the bones together and provides stabilization. While this can be accomplished in a minimally invasive fashion, it can create other, structural issues. The bones may be more susceptible to fracture and if the holes are misaligned, there could be issues with the suture sawing into the bone tunnel.

Passing instruments exist for circumventing bones. A typical instrument for passing a wire or suture under the coracoid or clavicle bones is a generally "C-shaped" hollow needle type or corkscrew type device as described by Whiteside (U.S. Pat. No. 5,501,688). It is often inserted adjacent the bone, then turned axially such that the curved portion is positioned under the bone. A flexible wire is then passed through the lumen to complete the pass. While these types of passers work well for circumventing a bone in the fully open surgical setting, they are very difficult to use in confined space as in a minimally invasive procedure.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

Embodiments proposed herein solve the above issues by providing a joint stabilization (reduction) system and associated methods and tools for placement of the system in an open or minimally invasive technique. In embodiments, the joint stabilization system includes a flexible band-like prosthesis (hereafter referred to as "prosthetic band") for stabilizing the bones in proper position and a connector mechanism (referred to at points herein as "Connector" or "Buckle") for joining the two ends of the prosthetic band around the bones. One end of the prosthetic band can be permanently attached to the connector.

Also disclosed herein as part of the system are tools that allow the placement of the prosthetic band around the bones in a minimally invasive fashion. Such proposed tools include a subset or all of: (1) a passing device (herein referred to at points as "Passer") which enables a passing suture construct to be threaded under bones, such as the clavicle and the coracoid, though a small incision or portal; (2) a countertraction tool for facilitating tightening of the connector; and (3) a punch tool for activating a locking feature of the connector. These tools can be used with the associated prosthesis/connector construct, allowing a minimally invasive stabilization of a joint separation.

In surgical procedures to repair or stabilize the AC joint and other joints, some goals of an implant prosthesis can be to reduce the separation (i.e., pull the displaced clavicle bone closer to the acromium and coracoid bones; also called "reduction") and to stabilize the bones in that reduced position, because the native ligaments are unable to do this job due to injury. The proposed prosthetic band of embodiments is a wide band of suture material with strength equal to or greater than the native ligaments. The great width of this prosthetic band relative to typical suture strands allows the forces pulling the two bones together to be distributed over a much wider surface area on the bones. This alleviates the danger of any "sawing" action on the bone due to a repetitive motion.

In an embodiment, varying degrees of reduction are achievable via the connector. To this end, connection of the two ends of the prosthetic band by the connector can be either temporary and permanent. In embodiments, the connector is permanently attached to one end of the prosthetic band and is configured such that the distal end of the prosthetic band can be removably attached to the connector, for example by threading the distal end through a slot in the connector and securing the distal end under a cleat on the connector, providing a temporary fixation/retention. The temporary fixation allows the surgeon to check the bone reduction to ensure its adequacy before permanently locking the connector, for example by deforming the cleat so as to lock the prosthesis in place. This embodiment is a one-piece design with no moving parts. Other embodiments of connectors providing both temporary and permanent fixations can include multi-part designs with sliding bars, clamping jaws, or rotating cam-lock mechanisms, as examples. The use of a buckle-type connector with a prong that pierces the prosthesis band is disclosed in yet other embodiments.

Other embodiments of connectors are disclosed herein which are not buckle-like. For example, a plate-like device can be utilized which lies across a section of the clavicle and anchors the opposing ends of the prosthetic band. By placing attachment points to the plate-like device at about a 20 mm separation, the prosthetic band may be affixed in an anatomical configuration. In embodiments, temporary and permanent prosthetic band attachment features may be incorporated into the plate. In other embodiments, holes in the plate-like device may align with holes in the clavicle to accommodate placement of tendon graft.

Other embodiments of prosthetic bands are disclosed herein. In one embodiment the prosthetic band may be a thermoplastic cable tie-like device with an integrated one-way connector at one end. Other embodiments of the prosthetic band may include use of a hook-and-loop connection mechanism.

Tendon grafts are often used in AC and CC joint repairs to augment the native ligaments and may be used in conjunction with the prosthetic bands disclosed herein. Further, prosthetic bands disclosed herein may contain certain features to accommodate and facilitate the use of a tendon graft. Strategically-placed slits in the prosthetic band may allow a tendon graft to be placed with, though, or on top of the prosthetic band while still maintaining some contact with bone to allow tissue ingrowth. Another embodiment utilizes an open weave or a weave that is more open in strategic locations to allow tissue ingrowth.

Prosthetic bands and configurations are disclosed herein which facilitate an "anatomical repair". To this end, in embodiments, prosthetic bands and methods of installation described herein support the existing ligaments by placing a prosthetic(s) that mimics the natural structure and placement of the native ligaments, for example at the AC and CC joints. In embodiments, the prosthetic band attaches at two attachment points on the clavicle about 20 mm apart. For example, in one embodiment, a prosthetic band may attach at one point on the coracoid bone and diverge outward like a fan to the clavicular attachment points. In another embodiment, a singular, flexible construct is created which has a shape, such as an "X" shape, that is suited to create an anatomical repair. The center portion of the "X" rests under the coracoid bone, while the legs of the "X" create the clavicular attachment points by wrapping in front of and behind the clavicle and connecting over the superior surface of the bone. Other embodiments create an "anatomical repair" by placing a simple single prosthetic band in a very specific anatomical configuration using specific methods as described herein. These methods of creating an anatomical configuration may utilize special tools that are further described herein.

As mentioned previously, the surgical repair of dislocated joints tends to be invasive and is commonly done in an "open" surgical setting, requiring a relatively large incision and extensive tissue retraction. When used in combination with enabling surgical tools, disclosed herein, a minimally invasive, arthroscopically assisted, or even arthroscopic approach may be used for implantation of a prosthetic band.

Disclosed herein, is a passing instrument that allows the surgeon to pass a prosthesis or a passing suture around the deeper-lying bones. It is also useful for passing elements around more superficial bones in that it may require less soft tissue dissection and retraction. This passing instrument is particularly useful for facilitating the passage of a prosthetic band of the type disclosed with this application.

In embodiments, an elongated cannula of the passing instrument is placed adjacent the bone to be circumvented. A shape memory element (wire or ribbon) that has been preformed to a diameter similar to or smaller than the bone diameter is disposed in the lumen of the cannula. Inside the lumen of the cannula, the shape memory element is constrained into a generally straight configuration. The cannula is fixedly attached to a handle of the passing instrument that houses a structure for extending and retracting the shape memory element out the distal cannula tip. A passing suture construct is detachably affixed to the distal tip of the shape memory element and also to the extension/retraction element. When the shape memory element is extended with the cannula adjacent the bone to be circumvented, the shape memory element encircles the bone, carrying the passing suture construct along with it. The distal end of the passing suture construct may then be picked up on the other side of the bone using standard surgical instruments. The shape memory element is then retracted within the lumen so that the cannula may be safely removed from the body. In embodiments, the cannula may have one or more features that facilitate proper placement of the cannula alongside the bone. For example, a protrusion can be provided that engages a bone for alignment. Various embodiments of the distal shape memory element tip and passing suture configurations are disclosed.

In embodiments, the proximal or handle portion of the passing instrument may be configured as a pistol-grip. The mechanism inside the handle portion may be configured so as to push the shape memory element out of the distal tip of the cannula at varying increments. A return trigger is disclosed that is attached to the extending/retracting element at the proximal end of the shape memory element. This return trigger allows the user to retract the shape memory element back into the cannula and may be attached to a suture-anchoring element provided through a slot in the handle housing. In an embodiment, the suture-anchoring element is a spool around which the passing suture element may be wrapped. A suture retention feature may be disposed on the anchoring element and is designed to pinch or otherwise firmly but releasably grip the passing suture element.

It may be beneficial for the shape memory element to deliver the passing suture construct all the way around the bone and reattach it to the cannula or a suture-receiving feature thereon. Disclosed within this application are various embodiments of passing suture reconnecting configurations. A soft sock-like structure that forms a tight-fitting cap over the distal tip of the shape memory element is disclosed in one embodiment. The passing suture construct is threaded through the cap that, after circumventing the bone, is trapped and retained by mechanism on the cannula. Other embodiments of suture passing/grabbing mechanisms include magnets and/or hooks to accomplish the suture pass back to the cannula. Once the suture has circumvented the bone and is reattached to the cannula, the cannula may be retrieved with both ends of the passing suture construct intact, thus saving the surgeon time and effort.

In embodiments, the aforementioned passing suture construct can be placed partially or fully around the circumference of the bone. This passing suture construct can be used to pull the prosthetic band into place around/under/behind a given bone, and thus is not a suture in the traditional sense. It does not remain in the body as a permanent implant or perform any ongoing function such as holding tissue together. The passing suture construct can be a single suture strand with a small loop on each end. The loops at each end facilitate temporary attachment to the shape memory element and the extension/retraction mechanism as well as ultimately the prosthetic band. In other embodiments, the passing suture construct is one continuous loop of suture or a single strand with knots at one or both ends. Features to aid in retrieval may also be employed such as tabs, or shorter trailing suture strands.

In embodiments, various methods of supporting or stabilizing joints are disclosed. These various methods may include various configurations of the prosthetic band around the bony structures. For example, a single loop of the prosthetic band around two adjacent but separated bones is disclosed for stabilizing the joint and/or providing support to the injured ligaments. Other embodiments include a "Figure 8 configuration", and a "Double-Luggage-Tag" configuration, which involves two loops around the clavicle at distinct, separated points, and two loops around the clavicle at the same location.

In embodiments, a method of stabilizing the AC joint is disclosed. The method includes: 1.) inserting a shape memory passing device into the joint space and adjacent the coracoid; 2.) using the passing device, extending a shape memory element with a passing suture attached at least partially around the coracoid; 3.) retrieving the passing suture from the tip of the shape memory element and bringing the passing suture outside the joint space; 4.) using the passing suture construct to pull a prosthetic band into position around the coracoid and the clavicle; and 5.) fixedly attaching the two ends of the prosthetic band in a tensioned state so as to reduce the separation of the coracoid and the clavicle.

In other embodiments, methods for placing a passing suture element around a bone are disclosed. These methods include: 1.) insertion of a passing device into the joint space and adjacent the coracoid; 2.) incrementally extending a shape memory element at least partially around the coracoid, said shape memory element carrying a passing suture construct; 3.) detaching the proximal end of the passing suture construct from the shape memory element; 4.) retrieving the passing suture construct from generally the other side of the bone; and 5.) retracting the shape memory element back into the passing device.

For a more comprehensive understanding of the nature and advantages of the present invention, reference should be made to the ensuing detailed description and accompanying drawings.

BRIEF DESCRIPTION OF THE DRAWINGS

FIG. 27 is a perspective view of an embodiment of prosthetic band connector with a pivoting wedge arm locking mechanism showing the prosthetic band in place in accordance with embodiments.

FIG. 28 is a section view of an embodiment of prosthetic band connector with a pivoting wedge arm locking mechanism showing the prosthetic band in place in accordance with embodiments.

FIG. 29 is a section view of an embodiment of prosthetic band connector with a pivoting wedge arm locking mechanism showing the prosthetic band in place compressed by the wedge arm.

FIG. 30 is a perspective view an embodiment of prosthetic band connector with a double clamping mechanism in accordance with embodiments.

FIG. 31 is a section view an embodiment of prosthetic band connector with a double clamping mechanism shown with the prosthetic band in place in accordance with embodiments.

FIG. 32 is a section view an embodiment of prosthetic band connector with a double clamping mechanism shown with the prosthetic band compressed by the clamping mechanism in accordance with embodiments.

FIG. 84 is a schematic view in furtherance to FIG. 83 showing a shuttle placed around the femur with cerclage cable attached.

FIG. 85 is a schematic view in continuance if FIG. 84 showing the cerclage cable further pulled around a femur bone.

FIG. 86 is a perspective view of an embodiments of a cerclage tip designed to accommodate a shuttle loop.

FIG. 87 is a perspective view of another embodiment of a cerclage tip designed to accommodate a shuttle loop.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

The technology disclosed herein has a broad application in orthopedic surgery. Procedures supported by devices disclosed herein include: Acromioclavicular joint stabilization/repair; tibiofibular syndesmosis stabilization/repair; other orthopedic procedures wherein an injured joint requires stabilization or repair; or any situation where two bones are separated and require reduction.

Embodiments proposed herein are directed to a flexible band-like prosthesis, referred to as "prosthetic band," for stabilizing bones in proper position. After the prosthetic band is in place, a connector is used to join the two ends of the prosthetic band around the bones. One end of the prosthetic band can be permanently attached to the connector, with the other attachable to the connector, or both ends can be attachable.

Figure 1:
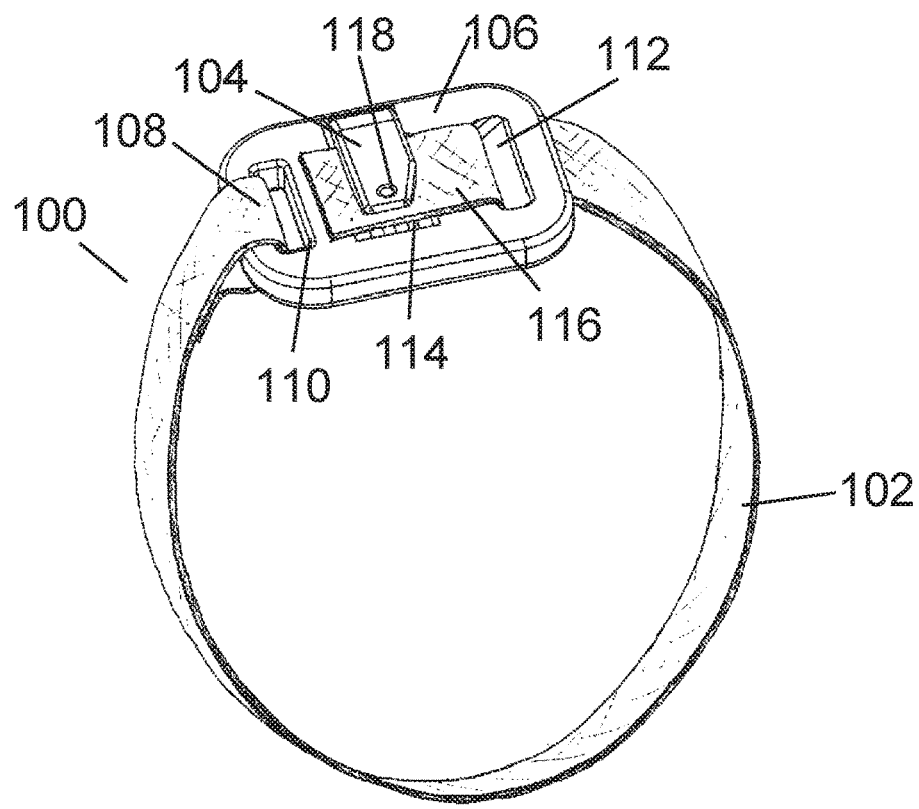
FIG. 1 is a perspective view of a prosthetic band assembly with a buckle-type connector in accordance with embodiments.

For example FIG. 1 is a perspective view of a prosthetic band assembly 100 with a wide flexible prosthetic band 102 and a connector mechanism 106. The band is significantly wider than a typical orthopedic suture strand or even suture tape (which is about 2 mm wide), and is typically 4 mm wide or wider. This extra width serves to distribute the loads seen by the band over a greater area of bone surface, thus reducing the risk of sawing into the bone due to repetitive motion. In the embodiment shown in the drawings, a proximal end 108 of the prosthetic band assembly passes through a slot 110 of the connector mechanism 106 and is fixedly attached back to the main loop of the prosthetic band by sewing, heat-staking or some other permanent attachment means. To connect a distal end 116 of the prosthetic band 102 to the connector mechanism 106, the distal end of the prosthetic band is threaded through a receiving slot 112 in the superior aspect of the connector and placed under a locking cleat 104. The locking cleat 104 protrudes from one side of the connector and extends over a locking slot 114, which may be a through slot or a blind slot, and which only extends through part of the total thickness of the connector. In its neutral or unactivated state, the locking cleat 104 extends roughly parallel to, or at a slight upward angle to, the superior surface of the connector and approximately across the full extent of the locking slot, and to the far end of the locking slot. This allows insertion of the distal end 116 of the prosthetic band under the locking cleat. When the distal end 116 of the prosthetic band is fed through the receiving slot 112, inferior to superior, and placed under the locking cleat in the unactivated or neutral state, temporary fixation is achieved.

To install the prosthetic band 102, the distal end 116 is extended through the receiving slot 112, and looped under the locking cleat 104. The relationship of the locking cleat and the leading and trailing edges of the locking slot 112 are such that the prosthetic band 102 is frictionally engaged by its serpentine path through the receiving slot 112, over the top of the connector 106, down into the locking slot 112, under the locking cleat 104, and back into engagement with the locking cleat and the top portion of the connector. The temporary fixation is achieved by friction at points of engagement of the prosthetic band 102 at these locations. Further information about this relationship is described with reference to FIGS. 16-18, where a similar buckle is described.

Temporary fixation generally requires a holding force on the prosthetic band greater than the force required to reduce the two bones being stabilized, which is generally associated with the weight of the patient's arm. This temporarily fixated state allows the surgeon to assess the positioning of the bones, possibly with x-ray or other visualization methods, to determine if reduction and positioning are adequate. If greater or less reduction or repositioning is required, the prosthetic band 102 may be readily removed from under the locking cleat 104 for further/less tensioning, etc. This process can be done in an iterative manner until proper tensioning of the prosthetic band assembly 100 is achieved.

Once the appropriate position of the prosthetic band assembly 100 and associated bones are achieved, the prosthetic band 102 may be placed into a more permanently fixed state within the connector 106 by permanently bending the locking cleat 104 downward with another surgical tool such as an orthopedic punch. This bending of the locking cleat 104 prevents further movement of the prosthetic band 102 relative to the connector 106, and fixes the loop formed by the prosthetic band assembly 100 to a fixed length.

To bend the locking cleat 104 down, an automatic center punch (not shown) can be used. An automatic center punch is a hand tool that is typically used to produce a dimple in a workpiece (for example, a piece of metal). It performs the same function as an ordinary center punch but without the need for a hammer. When pressed against the workpiece, it stores energy in a spring, eventually releasing the energy as an impulse that drives the punch, producing the dimple. The impulse provided to the point of the punch is quite repeatable, allowing for uniform impressions to be made. When used with the connector 106, the tip of the automatic center punch can be aligned with an indentation 118 on the locking cleat 104, and the automatic center punch can be pushed downward, storing energy into the spring until eventually firing the punch, which drives down, bends, and locks the locking cleat 104 into place. Thus, when pressed downward against the locking cleat 104 to a certain force level, the automatic center punch activates the spring mechanism which enhances the downward force to deflect the cleat. An automatic center punch typically makes an audible sound, indicating that the spring has been activated and thus may provide audible feedback to the surgeon that the locking cleat has been deflected to fix the prosthetic band in place. The spring release can typically be felt too, providing tactile feedback. Other lock-activation mechanisms may be used, with or without audible or other signals indicating activation. When the connector is placed in the locked or fixed position, the resulting construct (connector plus prosthetic band) may generally have an ultimate failure load equal to or greater than the native ligaments that are being augmented. In addition, the prosthetic band 102 is locked in place relative to the connector 106, assuring no further movement of the two relative to each other. The prosthetic band assembly 100 can then be sewn into the body through healing. Additional connector embodiments are disclosed later in the application.

Figure 2:
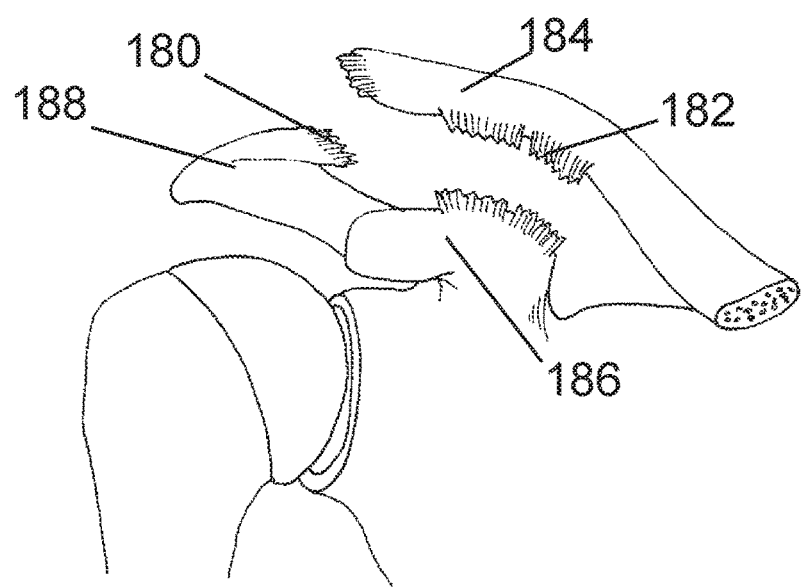
FIG. 2 is a perspective view of a dislocation acromioclavicular (AC) joint of a human body.

FIG. 2 shows a human shoulder joint that has a "separated shoulder" as described earlier in this application. The acromioclavicular ligaments 180 and the coracolclavicular ligaments 182 are severely disrupted. The clavicle bone 184 is shown displaced from both the coracoid bone 186 and the acromium 188. FIG. 2 represents an extreme case of this type of injury and is intended to show the bone displacement for simplicity and clarity. Most injuries don't involve complete severing of the ligaments as shown, but generally some level of damage one or both of the sets of ligaments shown. When damaged, these ligaments may stretch and become dislocated, and thus have a similar effect of allowing the clavicle bone to become displaced from the coracoid and or acromium. When surgically repairing a separated shoulder, augmentation of one of both of the ligamentous joints can effectively reduce the separation. For sake of simplicity and clarity, one or both sets of ligaments may not be shown in subsequent figures.

Figure 3:
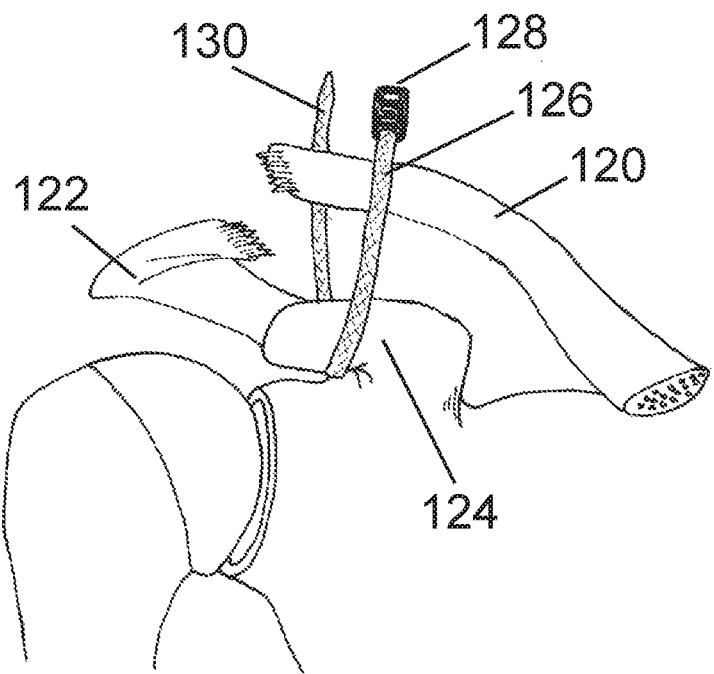
FIG. 3 is a perspective view of an open prosthetic band placed in the AC joint in accordance with embodiments.
Figure 4:
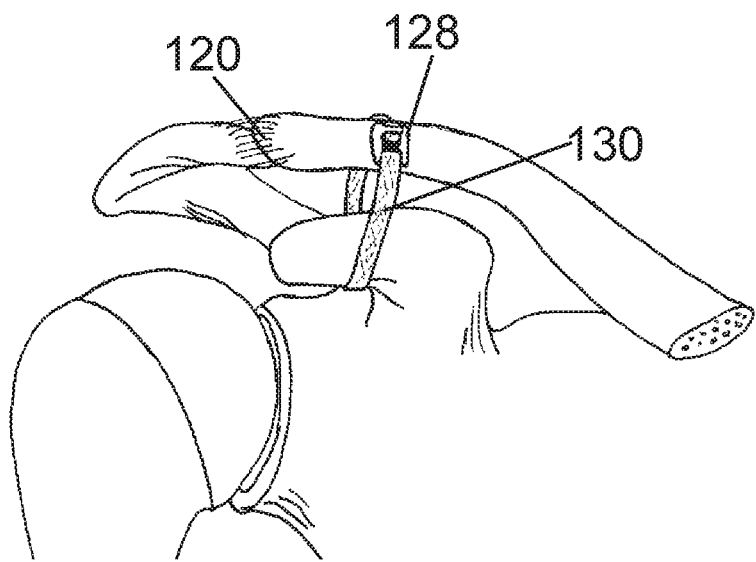
FIG. 4 is a perspective view of a prosthetic band in place and secured around the coracoids and clavicle bones in accordance with embodiments.

FIG. 3 shows an AC joint complex with a clavicle bone 120 displaced superiorly from the acromium 122 and the coracoid 124. A prosthetic band 126 (e.g., such as the prosthetic band 102) with a connector 128 (e.g., such as the connector 106) pre-attached to one end is shown looped under the coracoid and the distal, free end 130 of the prosthetic band on the opposite side of the clavicle from the connector. When the free end 130 of the prosthetic band 126 is threaded through the connector 128 and pulled or cinched as shown in FIG. 4, to create a taut loop, the clavicle bone is reduced back to a more natural position. In this simplified example, the prosthetic band 126 is serving as a proxy for the injured coracoclavicular ligaments (not shown), while also allowing the acromioclavicular ligaments 132 to heal in a more natural position. This is the most basic structural configuration of a prosthetic band assembly disclosed herein. Other configurations may be created using a single prosthetic band with connector, and many of those configurations are described herein.

Figure 5:
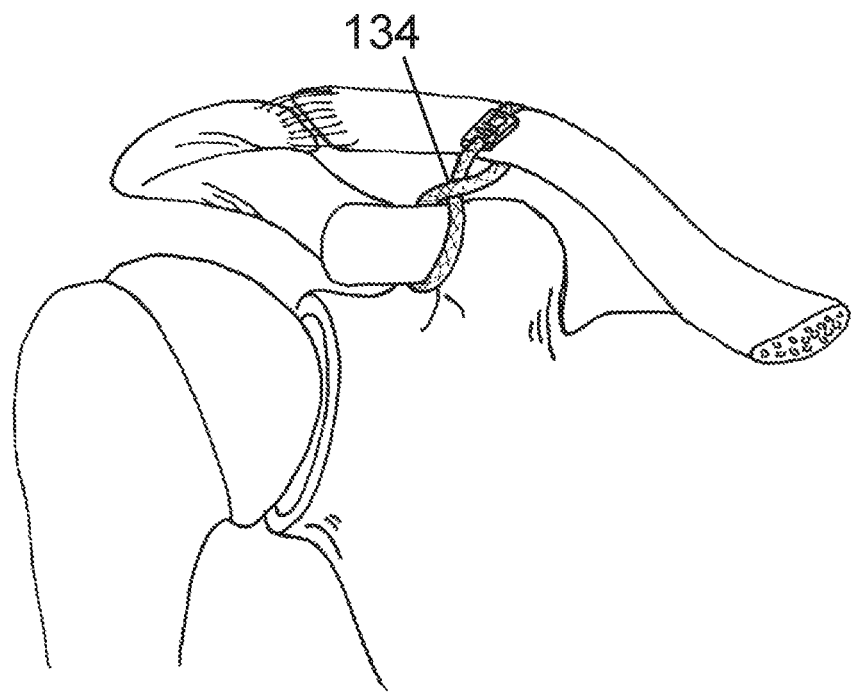
FIG. 5 is a perspective view of an alternate configuration of the prosthetic band in a "Figure 8" around the bones in accordance with embodiments.

FIG. 5 shows another configuration of a single prosthetic band with connector. The prosthetic band 134 (e.g., similar to the prosthetic band 102) is crossed over itself above the coracoid resulting in the loop reaching from the anterior side of the coracoid to the posterior side of the clavicle with the other leg doing the opposite. This type of configuration may result in better stabilization of the joint and allow less movement of the bones, particularly in the anterior-posterior direction.

Figure 6:
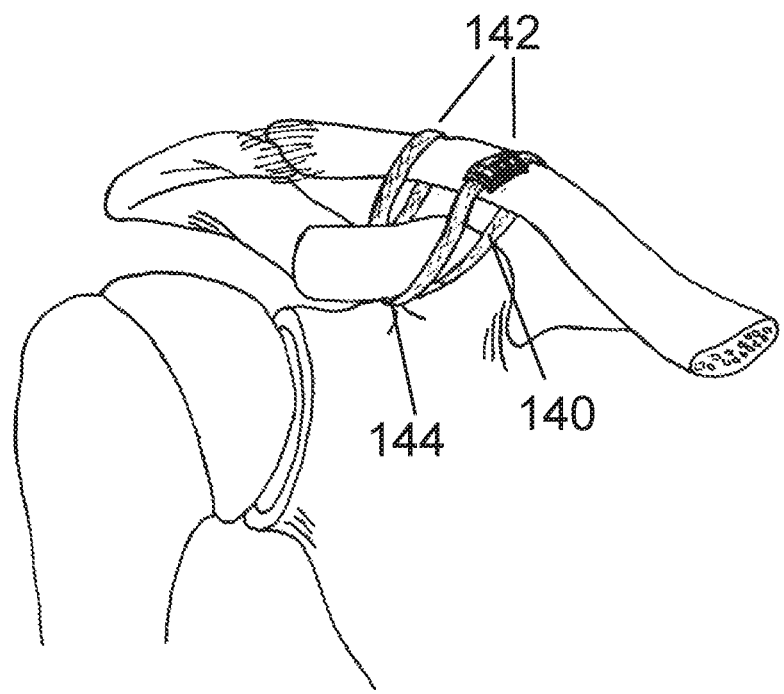
FIG. 6 is a perspective view of an alternate configuration of a prosthetic band in an anatomical configuration around the bones in accordance with embodiments.

FIG. 6 shows another configuration of a single prosthetic band with connector. In this "Double-Luggage-Tag" configuration, the single prosthetic band 140 (e.g., similar to the prosthetic band 102 but longer) is looped twice under the coracoid and around the clavicle. As such, two loops extend around the clavicle. In embodiments, the two loops are separated from each other by a particular separation 142, for example about 20 mm. As stated above, the prosthetic band also loops twice under the coracoid, but these two loops can be at essentially the same point 144 or adjacent one another. This configuration mimics the natural positioning of the coracoclavicular ligaments and may be considered an "anatomical repair" as known in the medical community.

Figure 7:
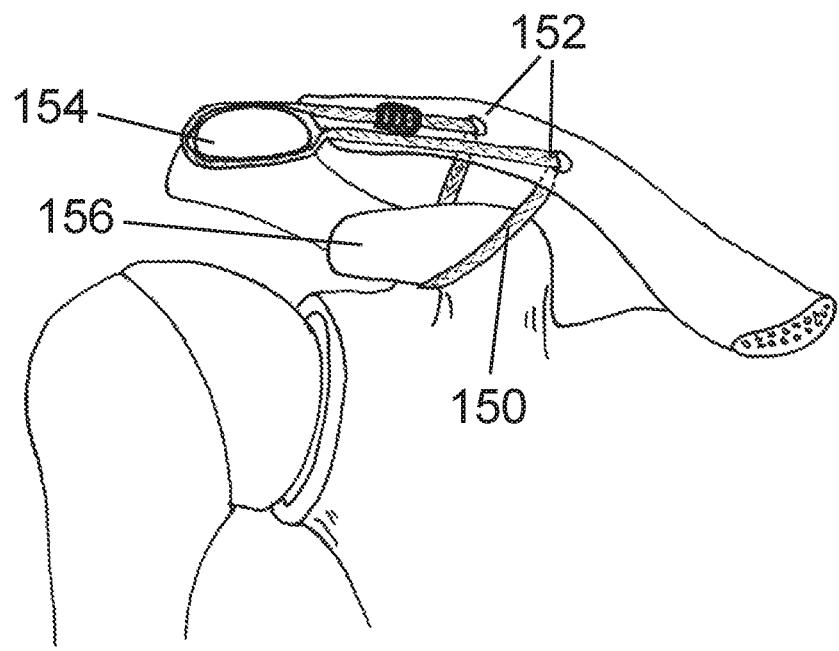
FIG. 7 is a perspective view of an alternate configuration of a prosthetic band in an anatomical configuration around the bones including the acromium in accordance with embodiments.

FIG. 7 shows yet another configuration of a single prosthetic band with connector. In this configuration, the single prosthetic band 150 (e.g., similar to the prosthetic band 102 but longer) loops under the coracoid 156 and is threaded through two clavicular bone tunnels 152, usually about 20 mm apart, and across to loop around the acromium 154. The two clavicular bone tunnels 152 are drilled by a surgeon during the installation process. This configuration mimics the natural positioning of the coracoclavicular ligaments as well as the acromioclavicular ligaments, and may be considered an "anatomical repair" as known in the medical community.

The embodiments of prosthetic bands disclosed thus far are flexible constructs fabricated from medical grade materials suitable for implantation in the body. In an embodiment, the prosthetic band is a woven polyester (PET) construct, however the prosthetic band could also be constructed by braiding from a variety of other suitable flexible biomaterials such as Ultra High Molecular Weight Polyethylene (UHMWPE) or blends or suitable materials. In embodiments, the prosthetic band is woven with metallic yarns such as stainless steel or nitinol. Various processes may be applied to the woven or braided band constructs to provide better performance characteristics. For example, heat treatment of band material after braiding can reduce the propensity of the weave to fray. Lack of fraying is particularly important to the "adjustability" aspect of the invention. After placing a prosthetic band and tightening it to reduce the bone dislocation, a surgeon may need to trim the excess material of the prosthetic band. Fraying at the point of trimming may reduce the effectiveness of the device.

Figure 8A:
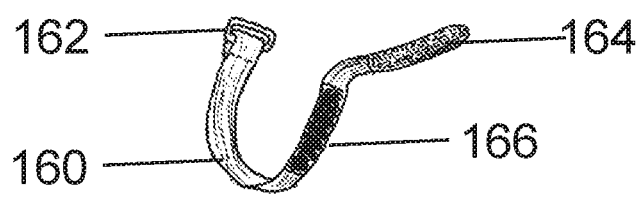
FIG. 8a is a perspective view of an open prosthetic band assembly having a hook and loop closure in accordance with embodiments.
Figure 8B:
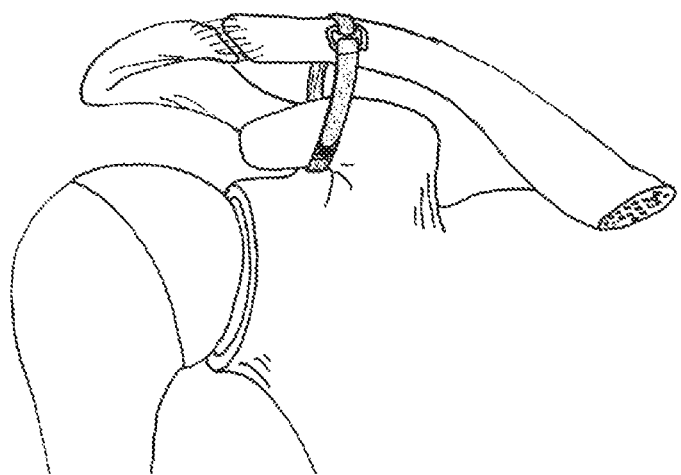
FIG. 8b is a perspective view of the prosthetic band assembly of FIG. 8a secured in place around the coracoids and clavicle.

In embodiments, other prosthetic band materials and other connection mechanisms may be employed. FIG. 8a shows a single loop prosthetic band 160 of a similar woven construct as previously disclosed. The simplified, pre-attached connector 162, however does not have an integrated locking feature as previously disclosed. Rather, a hook-and-loop connection mechanism is utilized. The distal end of the prosthetic band 164 is disposed with loop portion of the hook-and-loop connector while the hook portion 166 is strategically placed along a portion of the band. After looping the bones and threading the distal tip of the band through the connector slot, it is doubled-back over and attached to the hook portion on the band to form a permanent connection as shown in FIG. 8b. The hook and loop connectors can provide both temporary and permanent fixation of the prosthetic band.

Figure 9A:
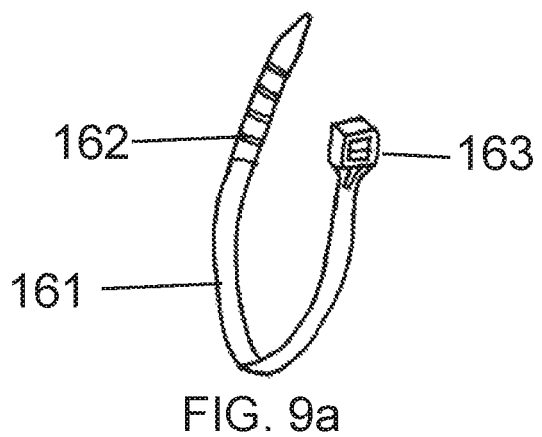
FIG. 9a is a perspective view of an a cable tie type prosthetic band assembly in accordance with embodiments.
Figure 9B:
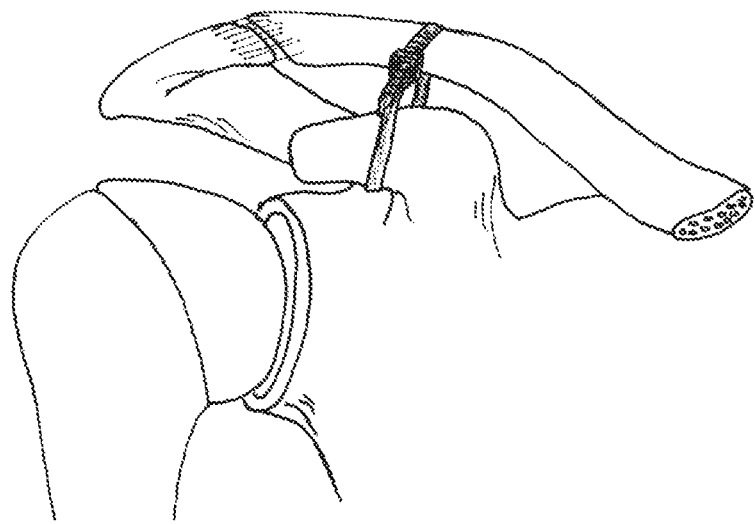
FIG. 9b is a perspective view of a cable tie type prosthetic band in place around the coracoids and clavicle in accordance with embodiments.

In accordance with additional embodiments, a single band prosthesis may be provided with an integrated connector. For example, FIG. 9a shows a single band prosthesis 161 configured similar to a cable-tie device. The prosthetic band has an integrated connecter 163 at the proximal end and a distal tip 162 configured with notches, fenestrations, bumps, grooves, teeth or other features so as to catch on a lock arm within the integrated connector on the proximal end. When placed in the AC joint as shown in FIG. 9b, the device may be tightened by pulling the distal end through the connector until the desired reduction is achieved. An integrated lock arm in the proximal connector can be provided to prevent the distal portion from sliding backward and loosening. This embodiment can be tightened further, but typically cannot be loosened once installed, so the temporary fixation features described above are provided only to the extent that further tightening of the single band prosthesis 161 is desired.

Figure 10A:
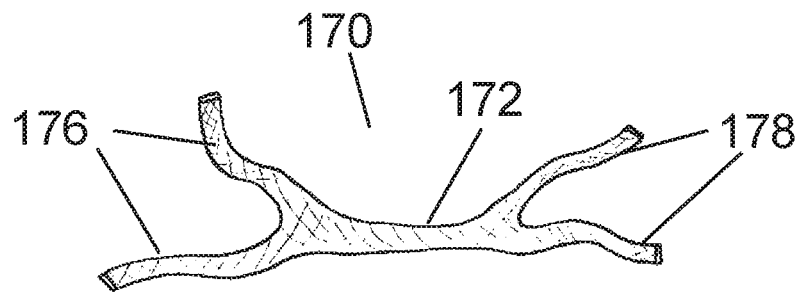
FIG. 10a is a perspective view of a custom-shaped anatomical prosthesis for AC joint stabilization in accordance with embodiments.
Figure 10B:
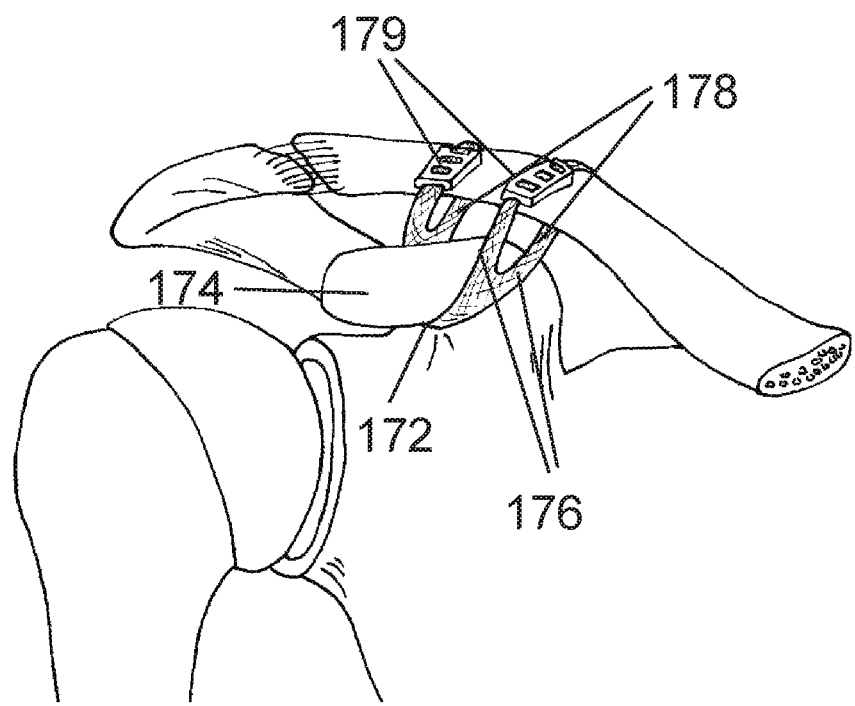
FIG. 10b is a perspective view of a custom-shaped anatomical prosthesis for an AC joint secured in place around the clavicle and coracoid in accordance with embodiments.

Ligament prostheses other than the single-band variety as discussed thus far are disclosed herein. In an effort to create an anatomical repair as defined previously, a specially-shaped prosthesis is proposed which inherently results in an "anatomic" configuration when implanted. FIG. 10a shows a generally X-shaped prosthesis 170 with a somewhat elongated center section 172. When placed in the joint space to stabilize the AC joint, the center section 172 is situated under the coracoid 174 with the two legs 176 of one side of the "X" joining over the top of the clavicle with the two legs from the other side of the "X". Connectors 179 as described elsewhere herein may be used to secure the corresponding legs to one another. The resulting configuration as shown in FIG. 10b represents a desirable "anatomic" configuration.

Figure 11A:
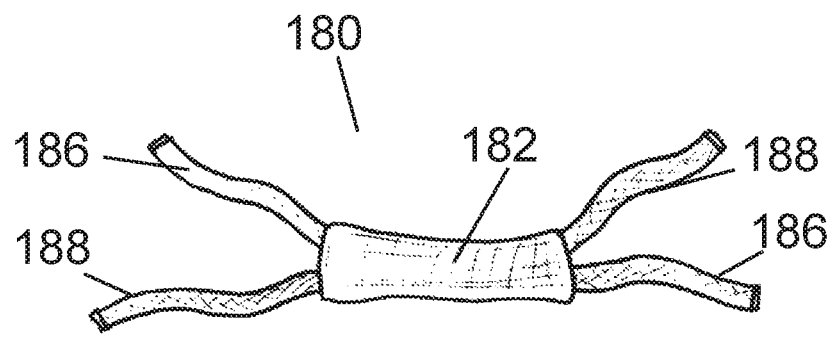
FIG. 11a is a perspective view of an alternative embodiment of an anatomical prosthesis for AC joint stabilization.
Figure 11B:
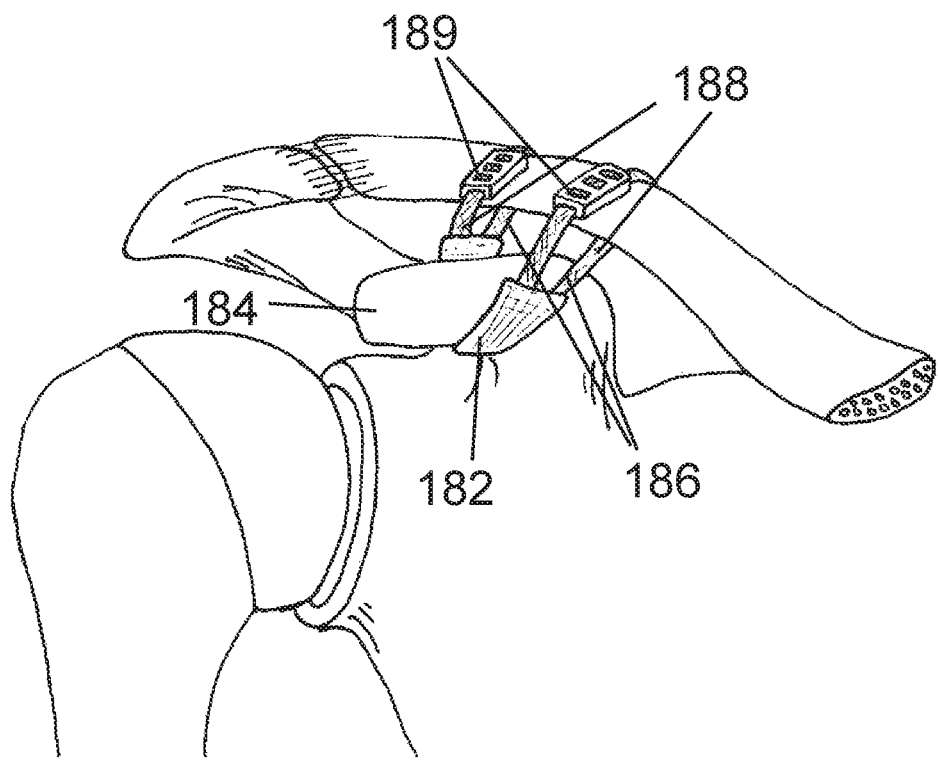
FIG. 11b is a perspective view of an alternative embodiment of an anatomical prosthesis for AC joint stabilization in place around the coracoid and clavicle of a human.

In another embodiment of an anatomically configured prosthesis 180, an "X" shape is created from multiple components. FIG. 11a show a generally "X" shaped prosthesis fabricated from two individual bands 186 and 188 connected where they cross at the center with a generally rectangular center piece 182. The rectangular center piece 182 maybe be a flat flexible woven or braided component or alternatively a tubular weave or braid. The flat variety would have the legs 186 and 188 fixed to one side by sewing, heat-staking, gluing or other construction technique or possible threaded through the yarns of the braided or woven center piece. Alternatively, the tubular center piece could allow the individual legs 186 and 188 to slide freely through lumen of the center piece. The legs may be anchored with connectors as described herein. When implanted in a joint as shown in FIG. 11b, one leg 186 starts at the anterior portion of the clavicle and loops under the coracoid 184, crosses the other leg 188 at the center piece and loops under the clavicle to the posterior part of the clavicle. The leg 186 would then connect to the other leg 188 via a connector 189 on the superior portion of the clavicle.

Thus far the connectors described for joining the ends of the prosthetic bands have been small devices appropriate for connecting two ends of the same band together at a single point or two ends of two bands together at a single point. Further connector embodiments include a somewhat larger plate-type connector that is capable of connecting single or multiple bands at the same point or at two distinct, separate points. In keeping with the "anatomic" theme, it may be desirable to have the two connection points separated by about 20 mm in order to mimic the native ligaments. The larger plate-type connector may also be conducive to the drilling of clavicular bone tunnels so as to allow the placement of a tendon graft. With clavicular bone tunnels being known to possibly weaken the clavicle, potentially resulting in fracture, the plate structure may provide support to the bone and/or act as a strain relief against the forces generated by the prosthesis and/or tendon graft. Ideally, a single loop prosthesis would share loading forces with the tendon graft that is placed through clavicular and plate-connector holes.

Figure 12A:
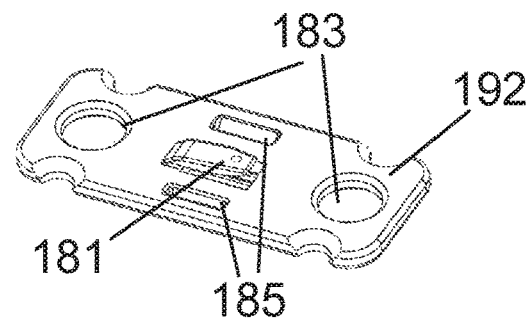
FIG. 12a is a perspective view of a plate-like connector in accordance with embodiments.
Figure 12B:
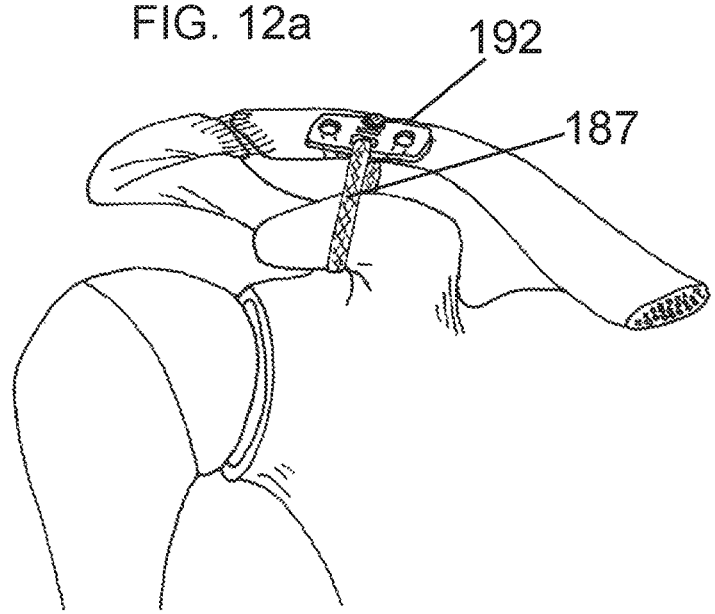
FIG. 12b is a perspective view of a prosthetic band assembly with the plate-type connector of FIG. 12a in place around the clavicle and coracoid of a human in accordance with embodiments.

For example, FIG. 12a shows an embodiment of a plate-type connector 192 with receiving slots 185 near the center and a locking cleat 181 between the slots. Holes 183 are configured at the distal ends of the plate for use with tendon grafts if desired. The plate-type connector 192 can be connected to the bone, for example by screws, adhesive or another suitable connector or connection structure. In this manner, the plate-type connector 192 can serve as a bone plate, stabilizing a fracture or preventing a fracture when bone tunnels are added. FIG. 12b shows the embodiment of FIG. 12a wherein two ends of a prosthetic band 187 are both attached to the plate near the center of the plate. One of the ends may be pre-attached during manufacturing with the other end being attached during surgery. The second attachment point may be the cleat locking mechanism described earlier, with both temporary and permanent locking modes.

Alternatively the second attachment point may be an attachment of any of the other attachment means, including, but not limited to, those disclosed herein.

Figure 13:
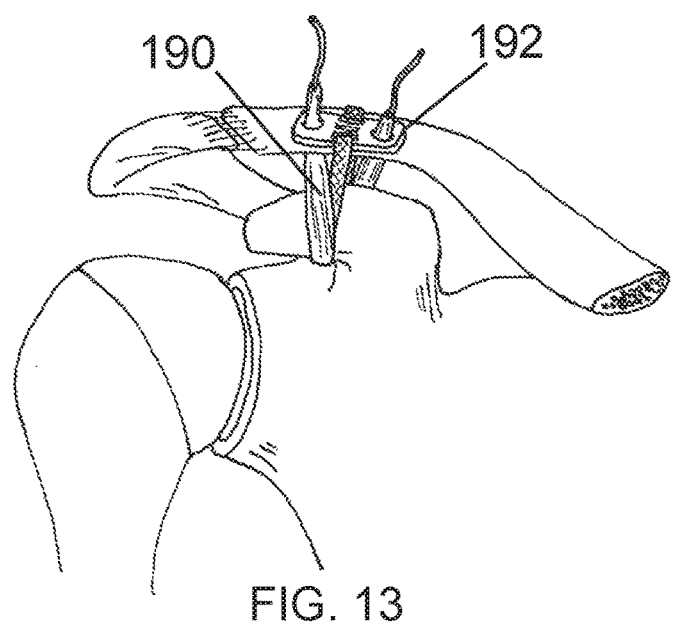
FIG. 13 is a perspective view of a prosthetic band assembly with a plate-type connector in place around the clavicle and coracoid with a tendon graft attached in accordance with embodiments.

The two holes at either end of the plate-type connector are positioned about 20 mm apart so as to provide an anatomic configuration when a tendon graft 190 is used as shown in FIG. 13. The tendon graft 190 loops under the coracoid and the two ends are threaded through the clavicular bone tunnels and as well as through the plate. The tendon graft 190 may then be secured by tying it to itself with knots or suture, or interference screws may be used.

Figure 14:
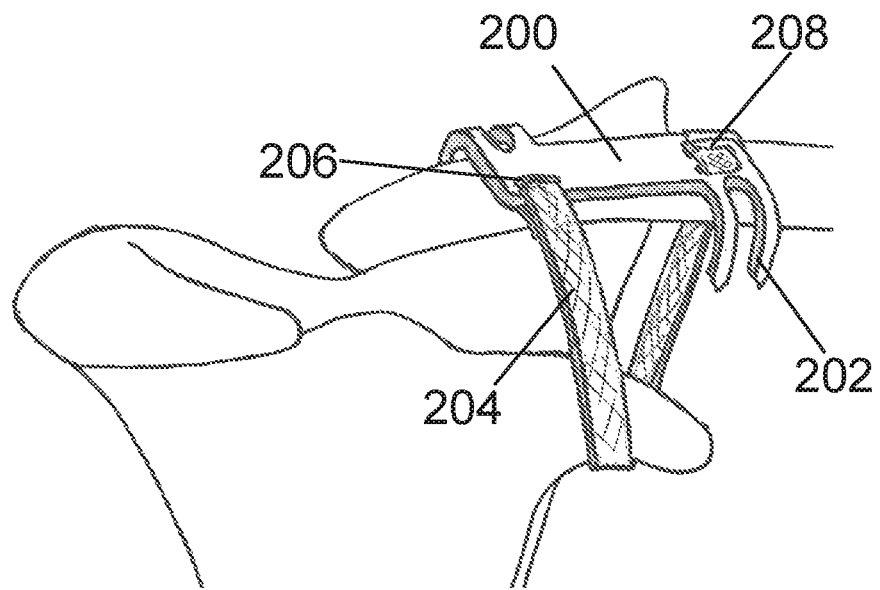
FIG. 14 is a perspective view of a prosthetic band assembly with a plate-type connector having self-locating flanges in accordance with embodiments.

FIG. 14 shows an embodiment of a prosthetic band 204 with an alternate embodiment of a plate-type connector 200. This connector 200 includes flanges 202 at either end that protrude inferiorly over the sides of the clavicle to maintain proper placement on top of the clavicle. In embodiments, the flanges may be beveled or sharpened so as to penetrate into any soft tissue around the clavicle. The attached prosthetic band 204 is fixedly pre-attached through a slot 206 on one end of the plate-type connector with the other end of the band attached during surgery through slots 208 at the opposing end of the plate. This attachment at the opposing end of the plate-type connector 200 may be of the type disclosed in FIG. 1 or any other connector mechanism disclosed herein. Alternatively, the prosthetic band 204 may be placed independently, not pre-attached to the connector then attached during the surgical procedure by any of the attachment means disclosed herein.

Figure 15:
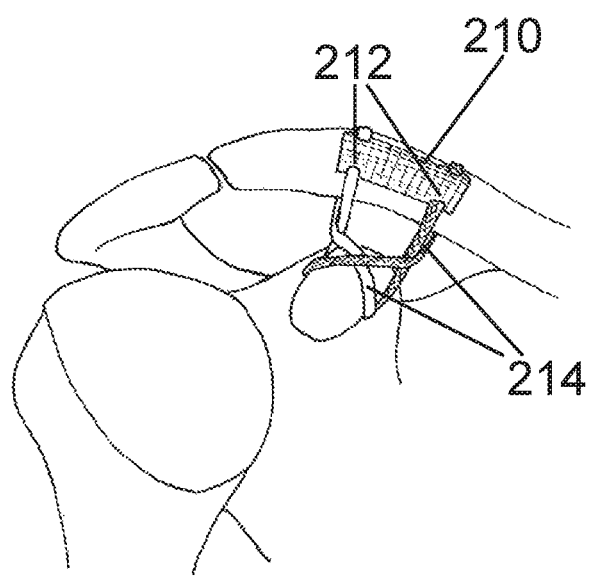
FIG. 15 is a perspective view of a prosthetic band assembly with a soft plate connector and a FIG. 8 band configuration in accordance with embodiments.

FIG. 15 shows an embodiment of a prosthetic band assembly with a soft plate-type connector 210. The plate-type connector of this embodiment is fabricated from woven, braided or molded biomaterials such as but not limited to PET or UEMWPE or nylon or like thermoplastics. Slots 212 in each end of the soft plate structure receive the free ends of the prosthetic bands 214 where the free ends may be sewn to the plate or attached via some other means. In embodiments, small metal or plastic connectors may be integrated into the soft plate during manufacturing to receive and lock the prosthetic bands into place. The two prosthetic bands 214 of the shown embodiment each cross over the coracoid to form a FIG. 8 before connecting on the plate at the superior aspect of the clavicle.

Figure 16:
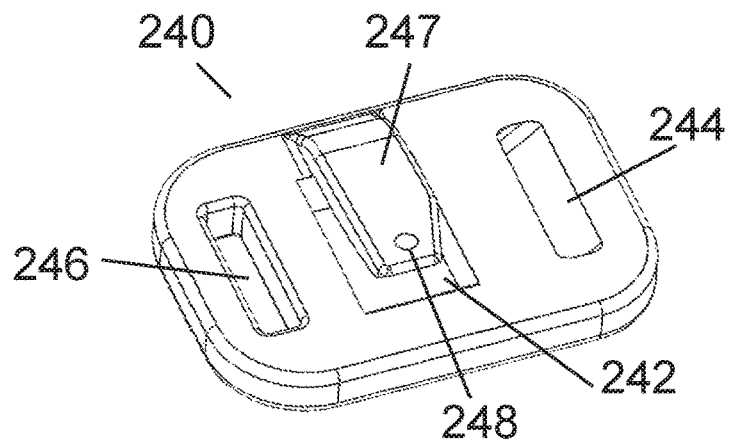
FIG. 16 is an embodiment of prosthetic band connector with a deflectable cleat locking mechanism in accordance with embodiments.

Returning now to the buckle-type connectors, FIG. 16 shows an embodiment of a connector 240 that is similar to the buckle-type connector of FIG. 1. As previously described, this type of one-piece connector has advantages in that it is simple in design, low in cost to manufacture, and easy to use. It also has both temporary and permanent prosthetic band retention capability. This embodiment of the connector 240 has an open locking slot 242, whereas the locking slot of FIG. 1 was a blind slot in that it did not go all the way through the connector. As in FIG. 1, this embodiment has an angled receiving slot 244 and a straight slot 246 where a prosthetic band may be fixedly attached. The locking cleat 247 has small dimple 248 that is intended to receive the tip of a manual or automatic center punch which is used to deflect the cleat downward into the locked position.

Figure 17:
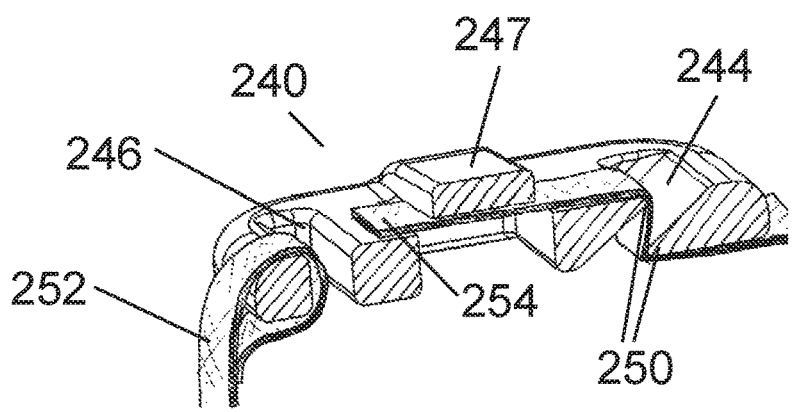
FIG. 17 is a section view of an embodiment of a prosthetic band connector with a deflectable cleat locking mechanism and the prosthetic band shown in place in accordance with embodiments.

FIG. 17 is a section view of the connector 240 of FIG. 16 with a prosthetic band 252 affixed. The prosthetic band 252 is shown fixedly attached at a proximal end through the straight slot 246. On the other end of the connector, the distal or free end 254 of the band 252 is fed through the angled receiving slot 244 then under the locking cleat 247. This represents the temporarily locked state, which is temporarily locked and unlocked as described above with respect to FIG. 1. As described with that embodiment, the band 252 may be removed from under the cleat 247 to unlock the band, tighten or loosen the band around the bones, and reset the band in the cleat to adjust the size of the loop made by the band and/or the tension applied by the loop. The temporary locking is achieved through the friction generated by the angled slot. Because of the angle it must navigate, the prosthetic band is prevented from sliding due to the friction on the edges 250 of the slot. The bottom surface of the cleat itself also provides some friction, as well as the band's engagement with the locking cleat, as described with reference to the embodiment of FIG. 1, above.

Figure 18:
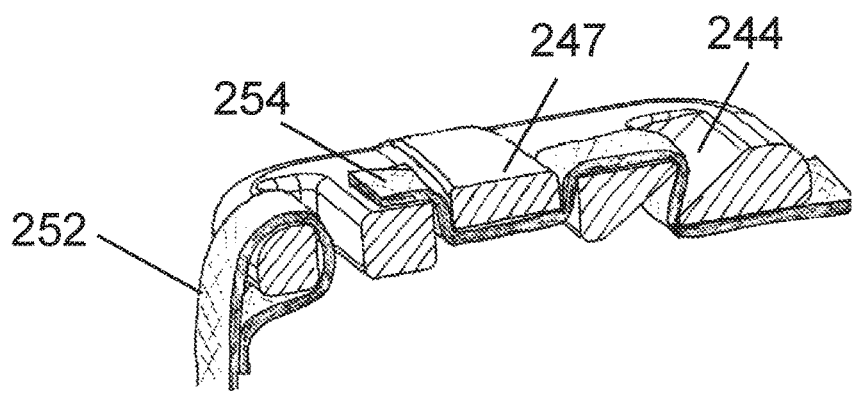
FIG. 18 is another section view of an embodiment of prosthetic band connector with a deflectable cleat locking mechanism and the prosthetic band shown in place, shown with the cleat deflected in the locked position.

In FIG. 18, the locking cleat 247 is show deflected into a downward position into the locking slot. In doing so, the prosthetic band is also forced downward into the locking slot, thus pinching the band and creating more corners with additional friction that must be overcome to unlock. This provides more permanent or irreversible fixation/retention. Any number of orthopedic tools may be used to deflect the cleat such as punches, clamps, needle drivers, etc. In an embodiment, as described above, an automatic center punch provide a repeatable deflection for to achieve the fixation. Use of such a punch further provides an audible and perhaps tactile indication to the surgeon that the cleat has been deflected. The dimple 248 may be used to align the automatic center punch with the locking cleat 247.

It is important to note that this embodiment as well as all other connector embodiments disclosed herein provides the capability of adjustment to the band tension around the bones. By feeding the band through a receiving slot on the connector and pulling the free end of the band while providing countertraction to the connector, band tension is increased. By virtue of the friction generated by both the receiving slot and the cleat, temporary fixation/retention is achieved. This allows the surgeon to assess the bone reduction, possibly by means such as x-ray, while the prosthetic band remains temporarily fixed. Temporary fixation of this nature must hold a force at least equivalent to the force required to reduce the bones (typically between 10 and 100 N). If additional adjustments are required, the prosthetic band is moved from under the cleat, allowing the band to slide within the receiving slot. Additionally, more permanent retention/fixation is provided by the connector (in this embodiment, by deflecting the cleat downward). This fixation would benefit from a holding force equivalent to or greater than the strength of the native ligaments being augmented, which is generally in the range of 450 N to 750 N.

Other buckle-type connector embodiments that provide the functions and benefits described above are disclosed. Referring back to the general buckle configuration of FIG. 16, additional features to this embodiment may be beneficial.

Figure 19:
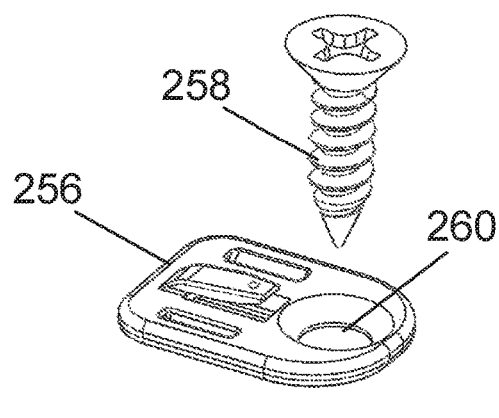
FIG. 19 is a perspective view of an embodiment of prosthetic band connector with a deflectable cleat locking mechanism configured to accept a screw for fixation to a bone.

FIG. 19 shows a buckle-type connector 256 similar to that of FIG. 16, with the addition of a feature in the form of a hole 260 allowing for the insertion of a small monocortical screw 258 or pin, which would anchor the connector to a surface such as the clavicle bone. Generally, the connector would be held in its relative position by the soft tissue surrounding the bones, however it may be beneficial prevent any movement of the connector in any direction. Said hole may be tapered or countersunk so as to allow the screw head to sit flush with the surface of the plate. A pilot hole may be drilled into the bone prior to insertion. In embodiments, connectors disclosed herein may be configured so as to accept one or multiple screw-type or other anchor retention mechanisms.

Figure 20:
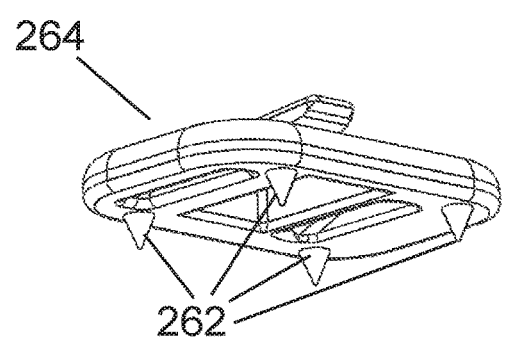
FIG. 20 is a perspective view of an embodiment of prosthetic band connector with a deflectable cleat locking mechanism configured with protrusion on the bottom surface for fixation to bone.

In FIG. 20, tapered protrusions 262 are shown configured on the bottom surface of a buckle-type connector 264. The protrusions 262 may be configured so as to penetrate the bone surface and prevent movement of the connector along the surface of the bone. The protrusions 262 may alternatively be configured, such as in low profile or high friction arrangements, so as to provide resistance to movement without penetration of the surface. In embodiments, one or more protrusions may be present. In other embodiments, undulations, corrugations, pits, grooves, knurling or other surface-disrupting features may be present on the bottom of the connector to provide resistant to movement.

Figure 21:
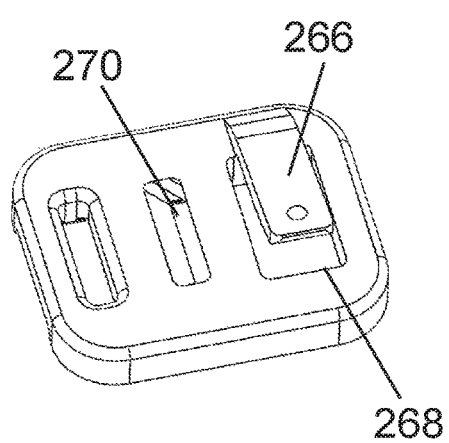
FIG. 21 is a perspective view of an embodiment of prosthetic band connector with a deflectable cleat locking mechanism configured with the cleat in the lateral position in accordance with embodiments.

In FIG. 21, another embodiment is shown of a buckle-type connector with a cleat. This embodiment is similar to the embodiment of FIG. 16, but with the cleat 266 and locking slot 268 moved to the end of the connector and the receiving slot 270 moved to the center. This connector embodiment provides all the same functions and advantages of the previous embodiment but with the locking cleat 266 on the end of the part, the direction of pull of the band through the receiving slot 270 at the center is toward the part end rather than the center. Given the surgical situation, this may provide a more convenient action for locking.

Figure 22:
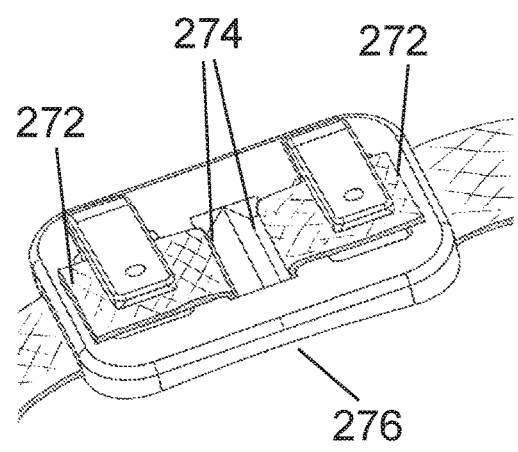
FIG. 22 is a perspective view an embodiment of prosthetic band connector with two deflectable cleat locking mechanisms in accordance with embodiments.

FIG. 22 is another embodiment of a buckle-type connector with two locking cleats. This connector embodiment provides all the same functions and advantages of the previous embodiment but does not have the prosthetic band pre-attached to one end. In order to achieve certain anatomical repair configurations with the prosthetic band, such as that of FIG. 6, it may be necessary to pull both ends of the prosthesis under the coracoid bone. This may be difficult to achieve with the connector pre-attached due to the friction caused by the surrounding soft tissue.

Therefore, the two free ends 272 of the prosthetic band may be passed and the connector assembled once the prosthesis is in position. The two free ends of the prosthesis are fed through the two receiving slots 274 near the center of the connector. One of the cleats is then deflected as described previously to lock the band in place. The other end of the band may then be used to adjust and/or tension the band construct in order to achieve appropriate bone reduction. Once achieved, the second cleat may be deflected to permanently fix the construct in place. This embodiment shows a curved bottom surface 276 of the connector to better approximate the shape of the bone. Alternatively, the entire connector may be curved to a degree that better matches the bone surface.

Figure 23:
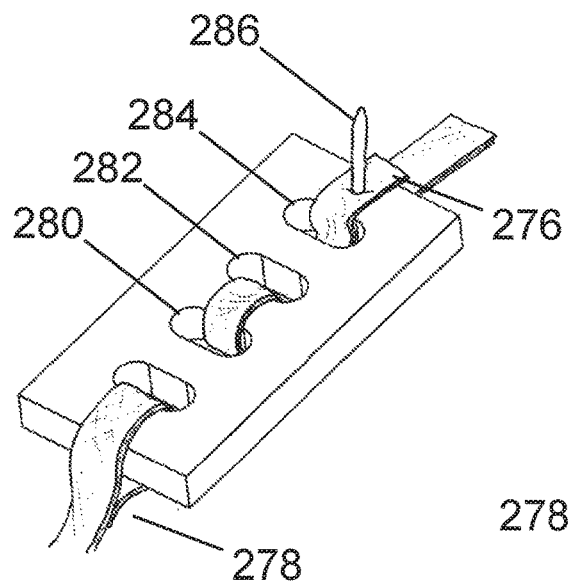
FIG. 23 is a perspective view an embodiment of a buckle-type prosthetic band connector with a prong retention mechanism in accordance with embodiments.
Figure 24:
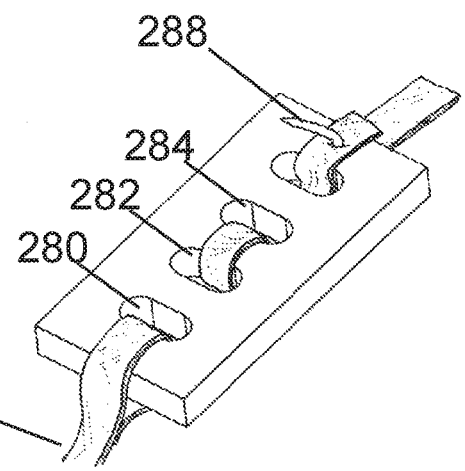
FIG. 24 is a perspective view an embodiment of a buckle-type prosthetic band connector with a prong retention mechanism shown deflected in a locked position in accordance with embodiments.

FIG. 23 is an embodiment of a simplified buckle-type connector. As with prior embodiments, a prosthetic band may be fixedly attached to one end 278 of the connector by sewing, gluing, heat staking or other assembly technique. The free end of the prosthetic band, after encircling the bones to be stabilized or reduced is fed up through the next available slot 280 then fed down through the adjacent slot 282 and finally returning up and out of the distal slot 284. At the distal end of the connector is a prong 286 configured to pass through the prosthetic band and effectively provide a permanent lock. The friction provided by the combined slot edges through which the band is passed as well as the prong provide a temporary fixation as described earlier so that the surgeon may assess for proper reduction. Because it may not be desirable to have a prong protruding upward into overlying soft tissue, the prong may be made of a material and configured so as to be deformable. FIG. 24 show the prong in a deformed state. The deformed prong 288 also ensures that the prosthetic band cannot be easily removed, thus forming a more permanent lock. When used with connectors of this type (prongs), the prosthetic band may be configured to have enhanced strength across the width of the band which resists the forces of the prong in the lengthwise direction. This may prevent the prong from effectively tearing through the band material. These strengthened sections across the width of the band may be created at discreet intervals so as to allow incremental tensioning of the band. Processes which may provide the bars or rungs of reinforcement include heat-staking and sewing of thick weft threads across the width.

Figure 25:
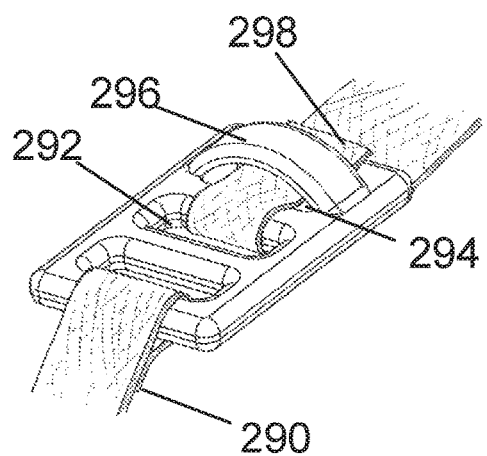
FIG. 25 is a perspective view an embodiment of a buckle-type prosthetic band connector with an alternative deflectable locking mechanism in accordance with embodiments.

FIG. 25 is another embodiment of a buckle-type connector. Like previous embodiments, one end of the prosthetic band 290 may be fixedly attached to the connector. The other end of the connector is configured with a receiving slot 292 and a locking slot 294. Over the locking slot 294 is an archway 296 of material which may be formed by a lancing operation. When the free end 298 of a prosthetic band is fed up through the locking slot then slipped under the arch, temporary fixation is achieved. By deforming the arch downward and thus forcing the band down into the locking slot, a more permanent fixation is achieved.

Figure 26:
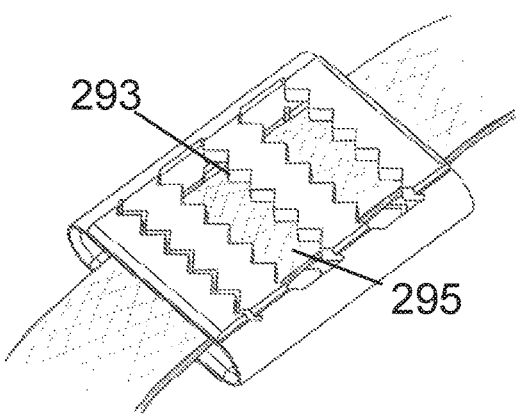
FIG. 26 is a perspective view an embodiment of prosthetic band connector that is configured as a crush tube in accordance with embodiments.

FIG. 26 is an embodiment of another connector for the prosthetic band. This is a simple crush tube configuration with opposing slots. When the ends of the prosthetic band are passed through the lumen of the tube either together in the same direction or in opposite directions, the tube may be crushed or flattened, effectively pinching and trapping the prosthetic band. To this end, the connector utilizes a crimping operation to close the connector. To provide this function, the connector is made of a deformable, self-holding material, such as metal. The opposing slot configuration allows for the band material to be forced into the open space 295 of each slot, and thereby being further retained by irregular edges 293 of the slots.

The connector of FIG. 27 has a main housing 300 with an open passageway or channel there through for the passage of the prosthetic band 302. While one end of the passageway is open, the other may be partially closed by a deformable gate 304. The gate may be configured with teeth 306 along the front surface to better engage the band. The gate may be configured so as to allow passage of the band in the direction of the gate, yet applying some compression to the band so as to make it difficult to pull the band in the opposite direction. At the other end of the connector, a pivoting, generally triangular-shaped arm 308 may rotate inward to apply compression to the band. The pivoting arm 308 is rotatably attached to the main housing 300, and is configured with teeth 310 resembling a gear or ratchet. The pivoting arm is also configured with a locking tab 312 which engages a window 314 on the main housing. Once fully engaged, the tab 312 snaps irreversibly into the window 314, and the prosthetic band 302 is permanently locked into place.

In the cut away view of FIG. 28, the band 302 can be seen lying in the channel with the pivoting arm 308 in a more or less neutral state. In this state, the band 302 is free to move in the direction shown by the arrow 303. FIG. 29 is another cut away view of the same embodiment as FIG. 28 in which the band has been moved in the direction of the arrow 305, which has engaged the pivoting arm 308 into a locking position. When the band 302 is moved in this direction, the teeth 310 at the leading edge of the pivoting arm 308 begin to engage the band and the further the band is pulled, the more the arm pivots to engage the band, in essence clamping tighter and tighter. This serves well as the temporary fixation discussed previously, in that the band is prevented from moving in the opposite direction by the tension normally placed on the band during installation. Thus, the band 302 does not loosen, and remains releasable by removing the tension in the band until the pivoting arm 308 is manually pushed in far enough to engage the lock mechanism (i.e., the tab engaging the window), at which point the band is permanently fixed in the fully engaged or clamped position as shown.

FIGS. 30-32 show an embodiment of a connector which has a double clamping mechanism. In FIG. 30, a housing 320 is shown with a channel 322 (best shown in FIG. 31) in center for passage of the prosthetic band 324. Two clamping tabs 326 are disposed in the sides of the housing with the flat part of the tab protruding out of slots 328 in the sides of the housing. The inner aspect of each tab is disposed with teeth 330 which may be disposed to be directional in nature. Each tab has two pins 332 that protrude upward from the tabs to engage angled slots 334 in the top and bottom of the housing. When the band is pulled in the direction of the angled slots (shown by arrow 331), the teeth on the tabs engage the band and the angled nature of the slots pulls the tabs toward the center, thus clamping tighter on the band. Like the embodiment of FIGS. 27-29, this is essentially a self-tightening mechanism in one direction of band pull. FIG. 31 is a cutaway view showing the tabs 326 in a neutral position. FIG. 32 shows the tabs 326 clamping on the band when the band is pulled in the direction indicated by the arrow. In embodiments the clamping tabs may be disposed with a tab lock as in the embodiment of FIGS. 27-29. The tabs may further be compelled into a locking position by squeezing them inward with a surgical clamp, forceps or the like.

Figure 33:
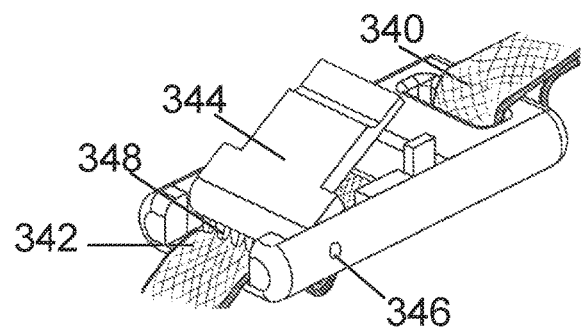
FIG. 33 is a perspective view an embodiment of prosthetic band connector with a pivoting cam arm retention mechanism in accordance with embodiments.
Figure 34:
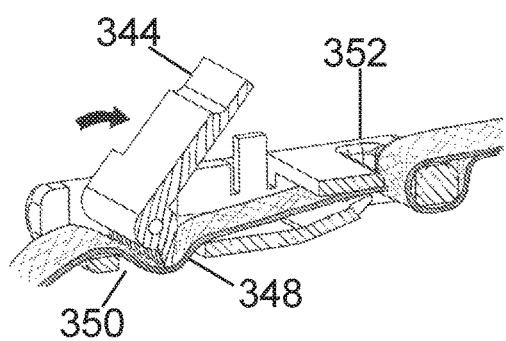
FIG. 34 is a section view an embodiment of the prosthetic band connector of FIG. 33 with a pivoting cam arm retention mechanism with the arm up.
Figure 35:
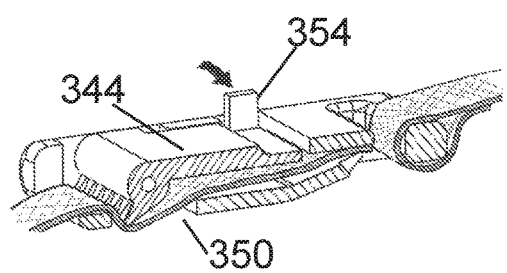
FIG. 35 is a section view an embodiment of the prosthetic band connector of FIGS. 33 and 34, with the pivoting cam arm retention mechanism having the arm down in the locked position.

FIGS. 33-35 show an embodiment of a connector with a cam lever locking mechanism. One end of a prosthetic band 340 may be fixedly attached to the connector as shown in FIG. 33. The other end of the connector has a receiving slot 342. Mounted to the housing just inside the receiving slot is a lever arm 344 with the pivot point 346 located in the middle of the housing just inside said slot. Disposed on the pivot at an angle to the lever arm is a locking cam 348 which may have teeth to better engage the band. In FIG. 34 a locking slot 350 is shown disposed in the bottom surface of the housing just below pivot. When the pivoting lever arm is in the upright position, a prosthetic band may pass through the receiving slot and under the pivot arm and out though a slot 352 on the opposite end of the connector. Once the band is appropriately positioned, the lever arm 344 is pivoted down in the direction indicated by the arrow which brings the locking cam 348 around, forcing it to push the band down into the locking slot. FIG. 35 shows the pivot arm completely closed with the locking cam fully engaged to trap the band in place. A final lock tab 354 may be folded down to permanently affix the lever arm in the locked position. Until this final lock tab 354 is deployed, the lever arm may be raised, allowing the band to slide again so that the tension may be adjusted. Again, this embodiment provides both a temporary lock and a permanent lock.

Figure 36:
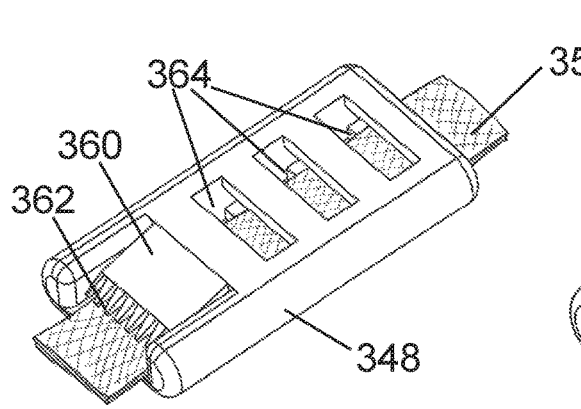
FIG. 36 is a perspective view an embodiment of prosthetic band connector with suture passing slots in accordance with embodiments.
Figure 37:
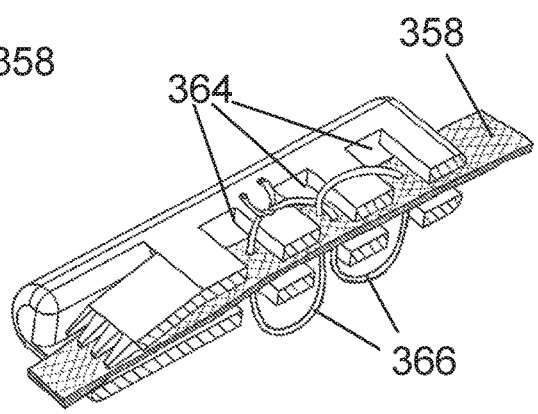
FIG. 37 is a section view of an embodiment of the prosthetic band connector of FIG. 36 with sutures in place to provide retention of the band in accordance with embodiments.

FIGS. 36-37 show an embodiment of a connector for securing a prosthetic band utilizing suture stitches through slots. A prosthetic band 358 or two ends of a band are passed through the central channel of the connector. A deflectable tab 360 with teeth 362 may be used to provide temporary fixation. The connector is disposed with one or more slots 364 through both the upper and lower surfaces of the housing. As shown in section view of FIG. 37, once the band is tensioned, typical orthopedic sutures 366 may be passed in and out through the slots and the sutures may cross from one slot to another. This suture stitching provides a permanent fixation.

Figure 38:
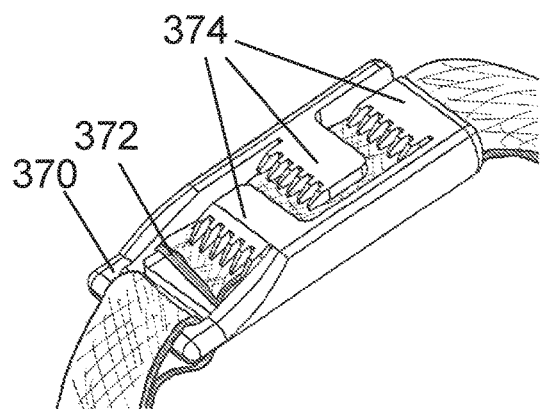
FIG. 38 is a perspective view an embodiment of a prosthetic band connector with alternating deflection tabs in accordance with embodiments.

FIG. 38 is yet another embodiment of a connector used to fix a prosthetic band. At one end 370 of the connector the prosthetic band is permanently fixed. The other end of the connector has an opening for a passageway that extends the length of the connector. The free end 372 of the prosthetic band is fed through the passageway and under a series of alternating deflectable flaps 374. In embodiments, one or more of the flaps may be deflected enough so as to contact the band to provide temporary fixation. Once the band is properly positioned and tensioned, the flaps may be deflected downward into the channel to pinch or trap the band. This provides permanent fixation.

Figure 39:
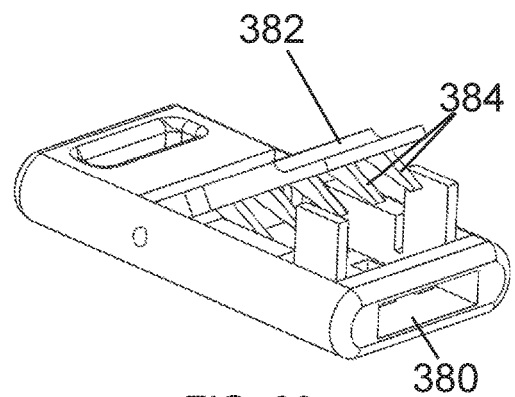
FIG. 39 is a perspective view of an embodiment of a prosthetic band connector with a toothed arm clamping mechanism in accordance with embodiments.
Figure 40:
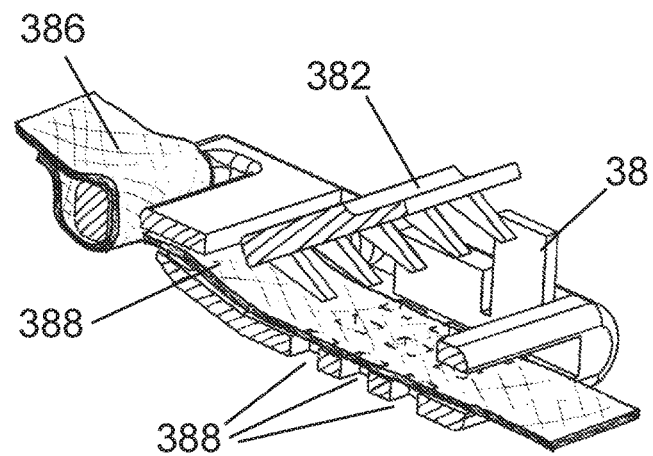
FIG. 40 is a section view of the prosthetic band connector of FIG. 39.

FIGS. 39-40 show another embodiment of a prosthetic band connector with a simple pivot arm retention mechanism. FIG. 39 shows a perspective view of the embodiment. Like previous embodiments, the connector housing is configured with a passage way 380 for passing of the band. A pivot lever arm 382 is show configured with multiple protrusions 384 for engagement of the band, though other embodiments may be configured with a single protrusion.

FIG. 40 shows a section view of the embodiment of FIG. 39. One end 386 of the band may be fixedly attached as in other embodiments. The free end 388 of the band is passed through the passageway opposite the fixed end when the pivot arm 382 is positioned up. When proper tensioning is achieved, the pivot arm 382 is rotated down to essentially clamp the prosthetic band, thus providing retention. The under surface of the pivot arm may be configured with protrusions which may be configured with pointed tips so as to better retain the band. Slots 392 may be configured on the bottom surface of the housing so as to receive the protrusions and band. Final or permanent locking may be achieved by deflecting the locking tab 390 downward, thus preventing the arm from moving.

As mentioned previously, when performing these AC joint repair/stabilizations and similar surgical procedures, doing so in a minimally invasive fashion is highly beneficial. To this point we have disclosed various implants for methods for stabilizing the bones and augmenting the ligaments. However, to place these implants in a minimally invasive fashion, specialized instruments are utilized. These instruments gain access to the deep-lying bones which are surrounded by soft tissue.

Disclosed presently, is passing instrumentation allowing a minimally invasive or arthroscopic approach to placing a prosthesis or a passing suture around both superficial and deeper-lying bones. The passing instrumentation disclosed is particularly useful for facilitating the passage of a prosthetic band of the type disclosed up to this point.

The prosthetic bands disclosed herein for stabilization and/or augmentation of the damaged ligament structures are placed around bony structures to avoid hole-drilling. In embodiments, instruments described herein provide access to the majority or all of a circumference of one or more bones, allowing installation of a band around the one or more bones. Gaining access to the underside of the bone, particularly deep-lying bones, is technically demanding. Further, gaining access to two sides of the bone in addition to the underside of the bone in order to place a prosthetic band is difficult to achieve.

Proposed now is an instrument designed with an elongated cannula for insertion into tight spaces and adjacent to one or more bones. The instrument utilizes a shape memory alloy element to circumvent a bone. Said shape memory element is designed to curve tightly around the bone while carrying a passing element which will be used to place the prosthetic band. In addition to curving tightly around the bone, the shape memory element maintains sufficient rigidity or stiffness to withstand the forces needed to extend through the soft tissue adjacent the bone. Such a passing instrument and associated elements are shown in FIGS. 41-46.

Figure 41:
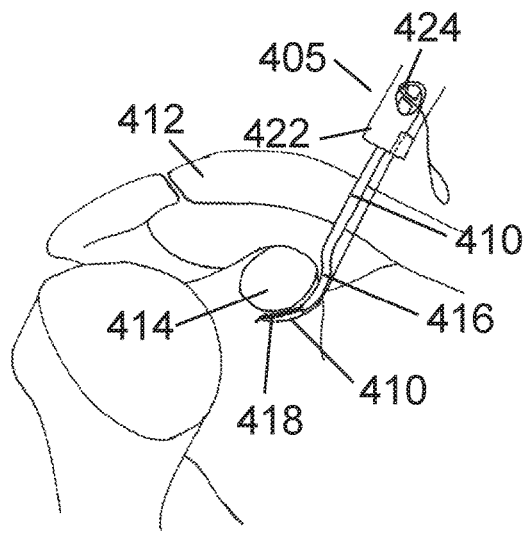
FIG. 41 is a schematic illustration showing the bones of the shoulder joint with a passing instrument inserted therein, in accordance with embodiments inserted.

FIG. 41 is a schematic illustration showing the bones of the shoulder joint with a passing instrument 405 in accordance with embodiments inserted. The elongated cannula 410 of the passing instrument 405 is placed alongside the clavicle bone 412 and abutted to the coracoid bone 414. The distal end of the cannula 410 may be straight or configured with a bone-location feature. The bone location feature of this embodiment is a curve 416 or bend at the appropriate position of the cannula so as to position the opening of the cannula at the optimal point on the bone for deploying the shape memory element. Other embodiments of bone-locating features are described in detail later. Shown protruding from the distal opening of the cannula is a shape memory element 418. This shape memory element 418 carries with it a passing element 420 which is releasably attached to the to the tip of the shape memory element. The shape memory element is compelled to exit the cannula tip by a translator located within the proximal housing 422 and operated by the user. The passing element 420 is releasably affixed at its proximal end to a return spool 424 that is internally affixed to the translator, such that when the shape memory element deploys out the distal tip of the cannula, the return spool 424 moves forward as well. This relationship allows the passing element to move forward with the shape memory element 418 as the shape memory element encircles the bone, while maintaining tension of the passing element 420 against the back of the shape memory element. Thus, tension that was initially created while attaching the passing element is maintained as the shape memory element is deployed.

Figure 42:
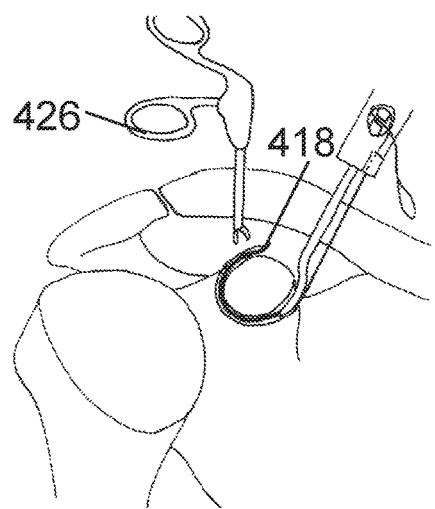
FIG. 42 is a schematic illustration showing the bones of the shoulder joint with the passing instrument of FIG. 41, with a shape memory element of the passing instrument further extended.

FIG. 42 is a continuation of this passing sequence. Here the shape memory element 418 is shown further advanced around the coracoid bone with the passing element in tow. To achieve this, the passing element 420 must typically remain in some tension along the back of the shape memory element 418 from the distal tip of the attachment of the passing element to the shape memory element to the proximal attachment of the passing element to the return spool. As described above, this function is provided by the tension that remains in the passing element due to the spool 424 moving with the shape memory element 418 as the shape memory element is deployed. In addition, the passing element 420 is further tensioned as the shape memory element 418 bends.

After the passing element 420 is extended around a bone, it is grasped and released from the shape memory element 418. A surgical grasper 426 or other appropriate surgical instrument is shown in position in FIG. 42 to retrieve the passing element 420. By deploying the shape memory element 418 substantially around the bone, the passing element 420 is then in a position to be retrieved from a port or superiorly located small incision. Alternatively the passing element 420 may be retrieved from a port more inferiorly or laterally located. This may require less deployment of the shape memory element 418 around the bone.

Figure 43:
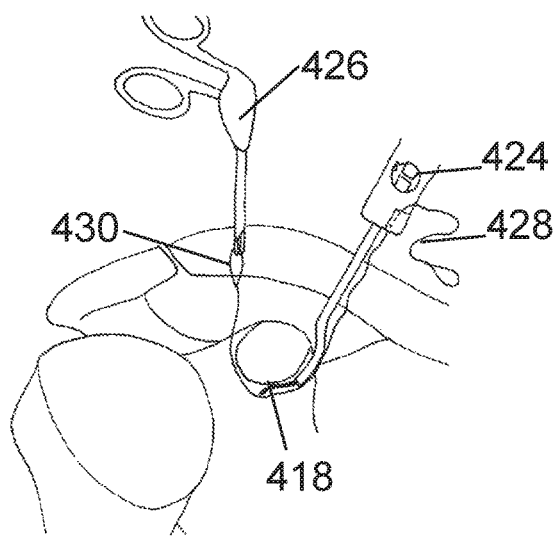
FIG. 43 is a schematic illustration showing the bones of the shoulder joint with the passing instrument of FIGS. 41 and 42, with a surgical grasper receiving a passing element from the passing instrument.

In FIG. 43, the proximal end 428 of the passing element 420 is shown detached from the return spool 424 to release the tension in the passing element, so as to allow for easier retrieval of the distal end 430 of the passing element. The surgical graspers or like instrument is shown in the process of pulling the passing element out of the body. The shape memory element 418 is shown in a partially retracted state.

After the passing element 420 has been retrieved, the shape memory element 418 may be fully retracted back in to the cannula 410.

Figure 44:
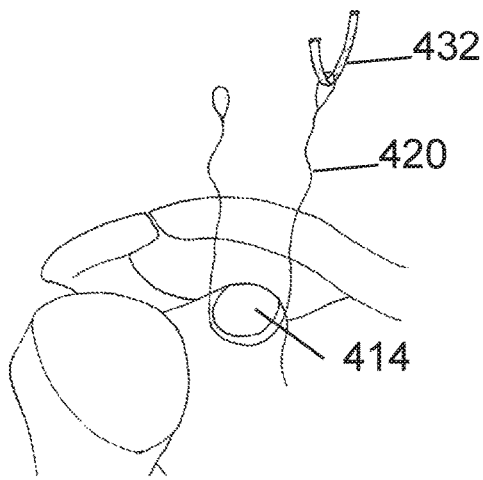
FIG. 44 is a schematic illustration, in furtherance to FIG. 43, showing the passing element pulled through the bones of the shoulder joint in accordance with embodiments.

In FIG. 44, the passing instrument 405 has been fully retracted from the body and the passing element 420 is positioned such that the central portion of the passing element is under the coracoid bone 414 and the two free ends exit the port or incision in close proximity. With the passing element 420 in place, other elements such as an implant or one or more additional passing elements may be attached to the passing element and pulled into the subcoracoid position. A prosthetic band 432, such as many of the bands described above, is shown inserted into the proximal loop 434 of the passing element 420, and is ready to be pulled into place.

Figure 45:
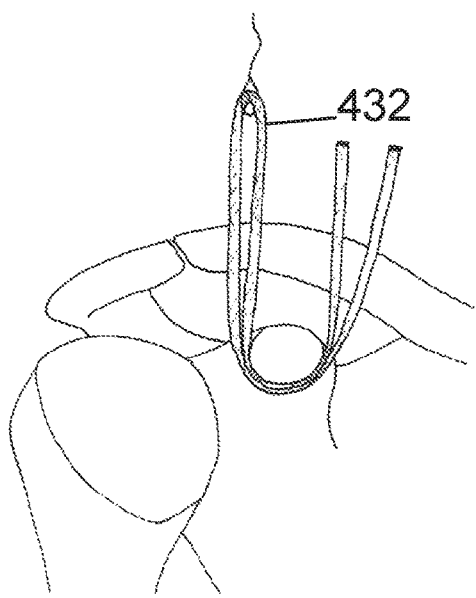
FIG. 45 is a schematic illustration, in furtherance to FIG. 44, showing the bones of the shoulder joint with a prosthetic band partially in place.

In FIG. 45, the distal end of the passing element has been pulled to drag the prosthetic band under the coracoid and superiorly above the clavicle. This embodiment shows the prosthetic band 432 fully doubled over. One of the ends may be pulled around under the coracoid if desired to result in a single band passage under the coracoid.

Figure 46:
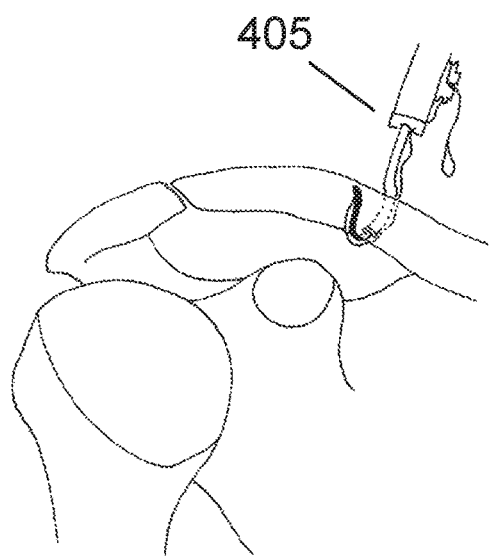
FIG. 46 is a schematic illustration showing the bones of the shoulder joint with a passing instrument partially deployed around the clavicle.

In FIGS. 41-45 demonstrate passage under the coracoid bone. Within the AC joint, the passing instrument and same passing method may be used to circumnavigate the clavicle as well. FIG. 46 shows the passing instrument 405 of FIGS. 41-45 being used to circumnavigate the clavicle bone.

Figure 47:
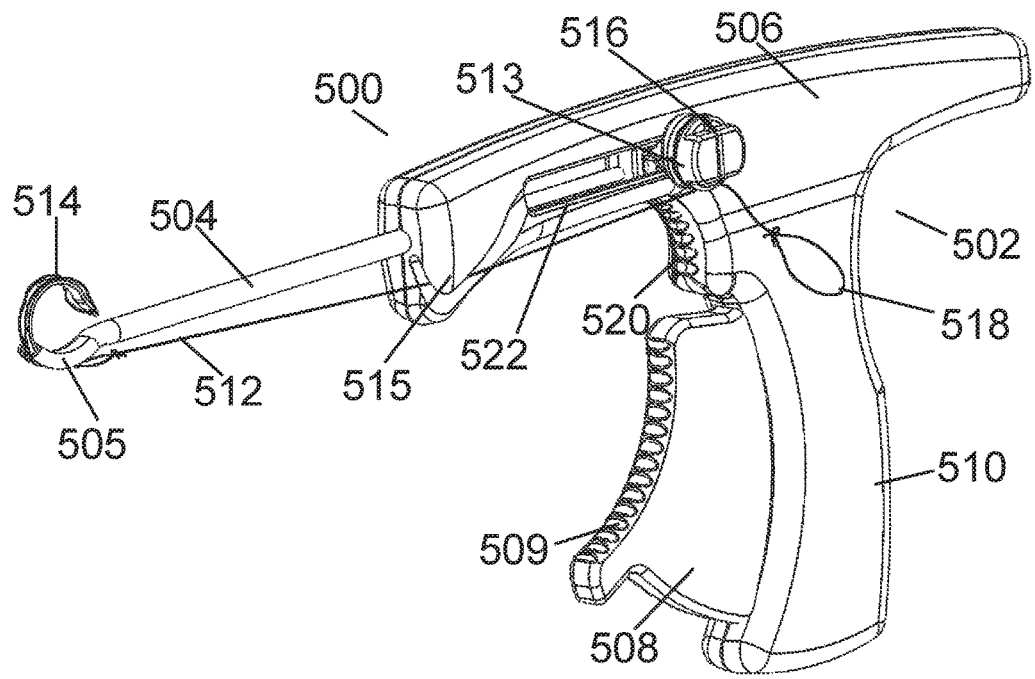
FIG. 47 is a perspective view an embodiment of a passing instrument with a passing element installed in accordance with embodiments.

In FIG. 47 is a perspective view of an embodiment of the passing instrument of the present invention. The generally pistol-shaped instrument 500 has a proximal handle 502 with a distal cannula 504 (e.g., the cannula 410) rigidly affixed thereto. As discussed previously, the distal end of the cannula 504 has a curve 505 incorporated which acts as a bone-location feature when the cannula is placed alongside a bone to be circumnavigated. The cannula 504 is of sufficient length to easily reach the deeper lying bones of a joint, typically 3" to 8" in length beyond a handle housing 506. The proximal portion of the handle housing 506 is generally shaped to be gripped in the palm with a large actuation trigger 508 extending from a vertical grip area 510. In an embodiment, the actuation trigger 508 may be configured with gripping features 509 which may be in the form of one or more bumps, grooves, undulations, slots, knurls, or other surface disruptions in an effort to enhance the users grip on the actuation trigger. A passing element 512 (e.g., the passing element 420) is situated on the device with its distal end releasably affixed to a distal tip of a shape memory element 514 (e.g., the shape memory element 418). The passing element 512 extends proximally to attach to a return spool 513 (e.g., the spool 424) disposed on the side of the housing 506. In an embodiment, the passing element 512 is a suture and is wound around the return spool in tension and pulled into a thin slot 516 on the front face of the spool, with any excess length 518 of the passing element 512 left to dangle. The thin slot 516 pinches the suture and provides secure retention. The return spool 513 is internally affixed to the return trigger 520 and is directed for sliding movement distally and proximally along a slot 522 in the housing. In embodiments, a guiding feature 515, such as an elongate groove, may be disposed at the distal end of the handle housing 506 in order to maintain the direction and location of the passing element 512 along the length of the distal cannula 504.

Prior to using the instrument to pass an element, the passing element 512 is affixed to the instrument as shown and the shape memory element 514 retracted fully into the cannula 504 by retracting the return trigger 520. When the passing instrument is abutted to the bone, the shape memory element is deployed out the distal tip of the cannula by pulling an actuation trigger 508.

Figure 48:
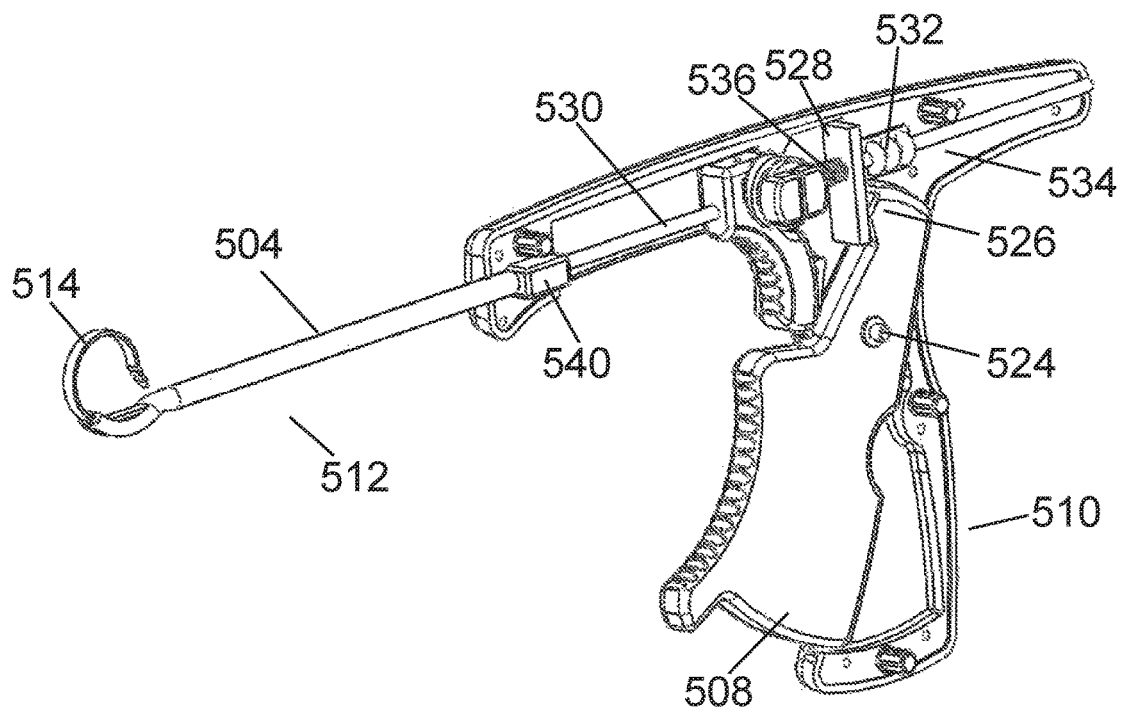
FIG. 48 is a perspective, cut-away view of the passing instrument of FIG. 47.

In FIG. 48 is a perspective cut away view showing the internal mechanism of the passing instrument of the embodiment of FIG. 47. In general, the passing instrument 502 is designed to work like a typical caulk gun, where the actuation trigger 508 is engaged to index the shape memory element 514 out of the cannula 504, and the return trigger 520 is engaged to incrementally retract the shape memory element 514. The shape memory element 514 includes a curve-biased distal end, which is flexible so that it can retract into a straighter position within the cannula 504, but resilient in that the distal end curves into its biased shape when the distal end is incrementally indexed outward from the end of the cannula 504. With each pull of the trigger 508, incrementally more of the shape memory element 514 is deployed out the distal tip of the cannula 504 and the distal end of the shape memory element returns to its generally circular, preformed, biased shape and specified diameter. Incremental deployment permits proper function and safe deployment of the shape memory element 514 around a bone. By pushing the shape memory element 514 forward in small increments, the surgeon can monitor the progress of the distal end and assure that the shape memory element is tracking properly around the bone. If it is determined that the shape memory element 514 is not tracking properly, the return trigger 520 may be used to retract the shape memory element for another attempt.

Additionally, the incremental deployment permits the shape memory element 514 to push through soft tissue surrounding bone a little bit at a time, and to determine whether bone is engaged during movement, so as to properly realign the tip of cannula 504. By contrast, if the shape memory element were pushed out quickly all at once, the tip is prone to catching in soft tissue and becoming stuck, while the rest of the shape memory element deploys in the improper location below the bone. The tip configuration, as discussed later, also enhances the ability of the shape memory element to pass through soft tissue and not drive directly into the bone and be stopped from further extension.

Returning to the trigger actuation, the actuation trigger 508 pivots around a pivot pin 524. An actuation rod 530 is affixed to the shape memory element 514 (best shown in FIG. 49) and is axially translatable within the cannula 504. A slide plate 528 is mounted on a proximal end of the actuation rod 530, and includes an opening therethrough. The opening is sized to receive the actuation rod 530 and hold the rod when the slide plate 528 is tilted or canted relative to the actuation rod, yet allow sliding of the rod through the opening when the rod is generally perpendicular to the plate. An actuation head 526 of the trigger 508 engages the plate 528 when the trigger rotates about the pivot pin 524. A plate spring 536 is mounted on the actuation rod distal to the slide plate 528 and proximal to the trigger 520.

Three O-rings 532 are seated around the actuation rod 530 in the rear part of the housing 534. These O-rings are trapped within ribs in the housing and thus not movable. Their purpose is to provide a retentive friction force against sliding movement of the actuation rod 530. This may be required because the radial force generated by the bias of the shape memory element compels the shape memory element forward and out the tip of the cannula. The O-rings provide enough friction to counteract the radial force of the shape memory element and prevent it from exiting the cannula tip of its own force.

An anchoring block 540 is rigidly fixed to the distal cannula 504. The anchoring block 540 is in turn immovably affixed in the housing 506 and has the purpose of providing a substantial connection means to the housing.

Figure 49:
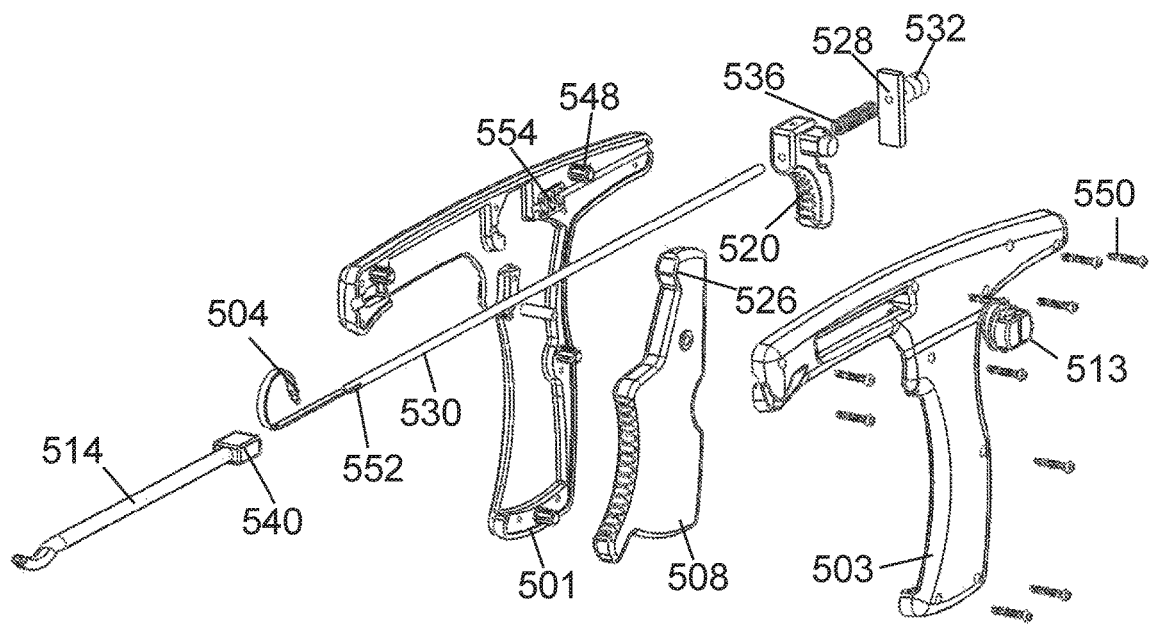
FIG. 49 is an exploded view of the passing instrument of FIG. 47.

FIG. 49 is an exploded view of the embodiment of FIG. 48, minus the passing element 512. In this view, a left handle housing 501 and a right handle housing 503 are shown, which when assembled together comprise the proximal handle housing 506. The handle housings 501 and 503 are held together with locator pins 548 which may provide a friction fit using a taper or deformable ribs. One or more screws 550 may be used in combination with or instead of the locator pins 548. A connection 552 is shown between the shape memory element 504 and the actuation rod 530. In an embodiment, the end of the shape memory element fits into a slot in the end of the actuation rod and is held there with a weld or adhesive. Pockets 554 in the left handle housing 501 accommodate the O-rings 532.

To propel the shape memory element 514 out of the distal end of the cannula 504, the trigger 508 is squeezed. The actuation head 526 pushes against the slide plate 528. When the trigger 508 is pulled and the actuation head 526 pushes against the bottom section of the plate 528, the plate is canted forward and by virtue of the hole also canting, the plate grabs the actuation rod 530 and pushes it incrementally forward. Since the actuation rod 530 is affixed to the shape memory element 514 and is axially translatable within the cannula 514, the shape memory element is pushed incrementally out the tip of the cannula. A typical increment distance may be in the range of 0.05" to 0.5", with optimal performance being achieved at around 0.1". When the trigger is released, the plate spring 536 pushes the slide plate 528 back to its starting point. This process continues to incrementally index the shape memory element 514 outward.

In embodiments, the passing instrument disclosed herein provides features that aid in appropriate positioning of a distal end of the cannula 504 (referred to herein as a "distal cannula") against the bone. In an embodiment, this is accomplished with previously disclosed curvature in the distal portion of the cannula 504. This configuration allows the user to abut the curvature against the side of a bone, which generally has a curved outer surface, thus providing the required position and stability of the cannula in relation to the bone. Disclosed now in FIGS. 50-52 are further embodiments of bone-locating feature related to the distal cannula.

Figure 50:
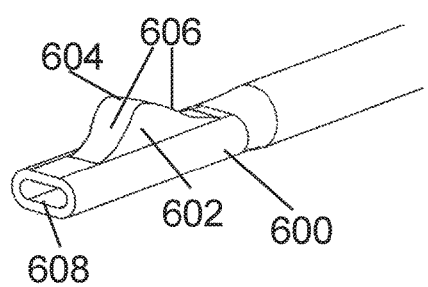
FIG. 50 is a perspective view of an embodiment of a distal cannula with a bone-locating protrusion accordance with embodiments.

FIG. 50 shows a generally straight distal cannula 600 with a bone-locating protrusion 602 configured on the outside of the cannula. This emdodiment of the protrusion 602 has a generally rounded top 604 and sloped sides 606. In embodiments, the protrusion may have straight sides and a flat or pointed top. The protrusion 602 is located at a distance from the opening 608 of the cannula, typically corresponding with the size of the bone(s) being circumnavigated.

Figure 51:
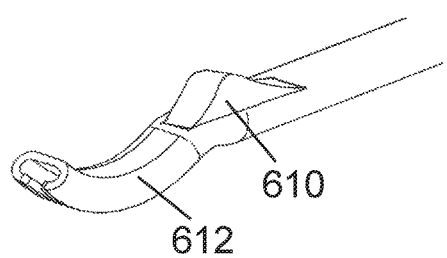
FIG. 51 is a perspective view of an embodiment of a distal cannula with a bone-locating protrusion and curvature in accordance with embodiments.

FIG. 51 shows a similar protrusion 610 to the one disclosed in FIG. 50 configured in combination with a curved cannula as disclosed in previous embodiments. The combination of both the curve 612 and the protrusion 610 may provide a better, more tactile, and stronger holding bone location function.

Figure 52:
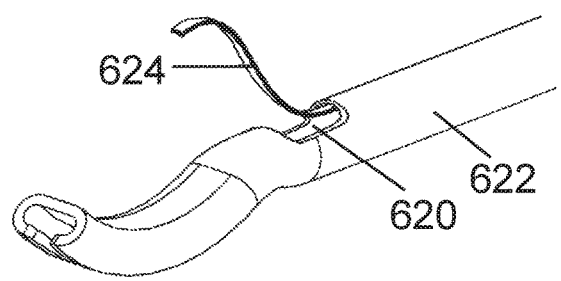
FIG. 52 is a perspective view of an embodiment of a distal cannula with a bone-locating prong in accordance with embodiments.

FIG. 52 shows another embodiment of a bone-locating feature. In this embodiment a slot 620 is configured in the distal canula 622. A resilient prong 624 eminates from the slot and is configured so as to abut a second surface of the bone to provide a stop. In embodiments the prong may be retractable into the cannula to provide a lower profile when inserting the passing instrument into tissue. In other embodiments the prong may be configured so as to temporarily flex or bend out of the way of tissue and other objects. The prong may be configured from metal such as stainless steel or nitinol or thermoplastic materials. In embodiments, the prong may also be affixed to the outer surface of the cannula or be formed from the cannula itself.

Also disclosed herein are features on the distal cannula to interface with the passing element. As described previously, the passing element may be detachably connected to the distal tip of the shape mory element (shown in FIG. 47). It is important when operating the passing instrument that the passing element remain in close approximation to the distal cannula and the proximal housing. This ensures proper alignment and movement of the passing element as it moves back and forth in the process of encircling a bone.

Figure 53:
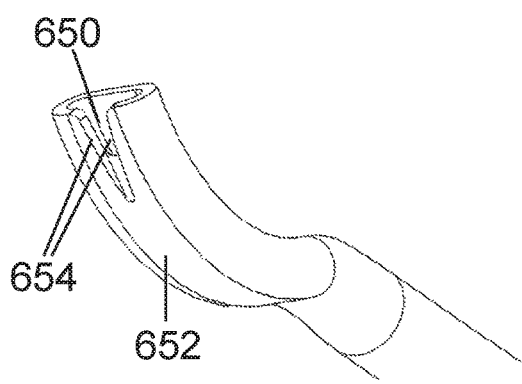
FIG. 53 is a perspective view of an embodiment of a distal cannula with a passing element control feature in accordance with embodiments.

FIG. 53 shows an embodiment of a passing element control feature. In this embodiment, the feature is a notch or slot 650 in the under side of the cannula 652. The slot is generally "V" shaped in the drawing, but it could be "U" shaped in alternate embodiments. When the shape memory element is deployed to any degree with the passing element releasably attached at the tip, the the passing element travels between the two sides 654 of the slot, keeping the element positioned in the center of the cannula and the center of the shape memory element. Thus, the slot provides proper operation of the passing instrument and keeps the passing element properly positioned throughout the passing operation. It should be noted that any of the disclosed passing element control features may be applicable to various embodiments of the cannula as well.

Figure 54:
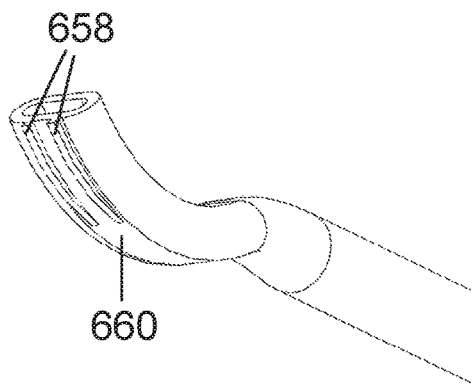
FIG. 54 is a perspective view of an alternate embodiment of a distal cannula with a passing element control feature.

FIG. 54 shows another embodiment of a passing element control feature. In this embodiment two ribs 658 protrude orthogonally from the distal cannula 660. The inner sides of said ribs serve to control the location of the passing element and guide it down the cannula in the same manner as the slot of the previous embodiment.

Figure 55:
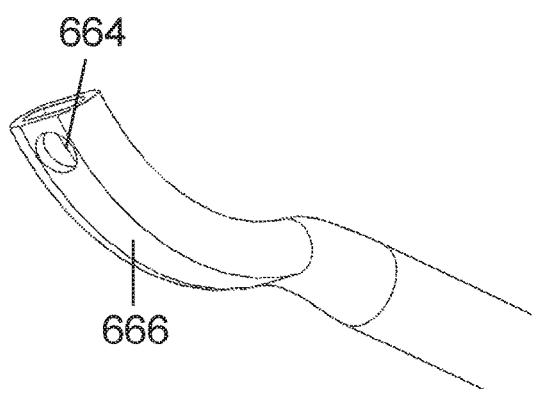
FIG. 55 is a perspective view of another embodiment of a distal cannula with a passing element control feature.

FIG. 55 shows another embodiment of of a passing element control feature. In this embodiment, a hole 664 is configured in the bottom surface of the distal cannula 666. The passing element is threaded into the hole which is sized such that the passing element readily fits through it, yet it maintains adequate control of the passing element.

As stated above, in accordance with embodiments, the shape memory element includes a curve-biased distal end, which is flexible so that it can retract into a straighter position within the cannula, but is resilient in that the distal end naturally curves into its biased shape when not under the influence of the cannula or other outside forces. Thus, when the shape memory element is incrementally deployed from the tip of the cannula as described previously herein, it assumes a generally circular or arched shape, facilitating its passage around a bone.

In an embodiment, the shape memory element is made of nitinol, although other materials can be used that have a resilient memory for returning to their original positions, are flexible so that they can straighten when needed, and are sufficiently stiff to penetrate soft tissue without bending excessively.

The need to straighten and then curl is a function of the tight working conditions of the procedure. In embodiments, as described above, the cannula is inserted orthoscopically, with a need for the cannula to be generally straight for directing the distal cannula to a bone. In contrast, the shape memory element needs to curve dramatically to circumnavigate the bone.

Applicants have found that to meet the above properties, a material should have sufficient elasticity to withstand repeated bending from its natural curved shape, to a flattened shape within the cannula, without failure. Otherwise, if flattened by the cannula, the shape memory element can have failures at molecular bonds, resulting in local or catastrophic breakages, and preventing the shape memory element from returning to its natural curved shape.

To extend into a hoop with a tight enough circle to circumnavigate a bone and then be able to straighten into a cannula, applicants have found that a material should have an ability to withstand elongation of at least 3%, and more preferably 5%, and most preferably around 8% or more.

In an embodiment, the shape memory element is made of nitinol, which typically has a maximum elastic strain of approximately 8%. As this 8% elastic strain limit is approached and exceeded, the shape memory element may not return fully to its intended preformed shape and thus not function properly for its intended purpose of encircling the bone. To achieve the curved shape in nitinol, the flat, elongate, generally straight piece of nitinol is constrained in the desired circular shape and brought to a temperature of approximately 500 degrees C. for a period of time, usually in the range of 10 to 20 minutes.

Applicants have also found that, for the shape memory element to penetrate soft tissue around the bone, the shape memory element must have sufficient radial stiffness. That is, the shape memory element must resist bending from its looped shape while being deployed around the bone. There is a significant amount of soft tissue around any given bone and it must be overcome by the stiffness of the shape memory element. In embodiments, the loop of the shape memory element is approximately equal to, or smaller than, the diameter of the bone to be circumvented. In this manner, the loop hugs the bone as it is extended to circumnavigate the bone. In an embodiment, a shape memory element loop diameter of 0.65" is formed with a ribbon of 0.03" thick and 0.112" wide for circling a coracoid bone. A thickness range of 0.015" to 0.06" may be appropriate for the proposed application combined with a width range of 0.05" to 0.25". The loop diameter may be appropriate in the range of 0.3" to 1", and functions more optimally when it is slightly smaller than the bone. Ideally the shape memory element should be as thick as possible without exceeding the strain limit of the material, however it must be noted that the thicker the material, the greater the resistance of the surrounding soft tissue to penetration. This may be at least partially overcome with an appropriate tip configuration, as explained later. In short, an element of optimal radial stiffness that does not exceed the post processing strain limit of the material combined with the appropriate tip configuration allows the passing of a shape memory element around a bone.

As indicated above, in embodiments, the shape memory element is constructed of nitinol, and as has been established has a preferred loop diameter, width and thickness in order to achieve appropriate radial stiffness. Another property that may impact the radial stiffness is the inherent Austenite Finish (Af) Temperature of the nitinol. This is the temperature at which the transformation from austenite to martensite finishes upon heating the material and is commonly used to specify a nitinol alloy. For the application described herein, an Af temperature in the range of −20° to 20° C. can be utilized. In order to achieve temperature below 10° C. an additional element such as Chromium may need to be added to the alloy. This alloy is known as Chromium Doped Nitinol and as a result of the lowered Af temperature, can increase the radial stiffness of the shape memory element. With this inherently increased stiffness, the thickness of the shape memory element may be lowered, while still maintaining a high radial stiffness for a given loop diameter. This allows for a thinner shape memory element of equal strength, thus providing functional advantages as the shape memory element pushes its way through soft tissue while circumventing a bone.

Figures 56, 57:
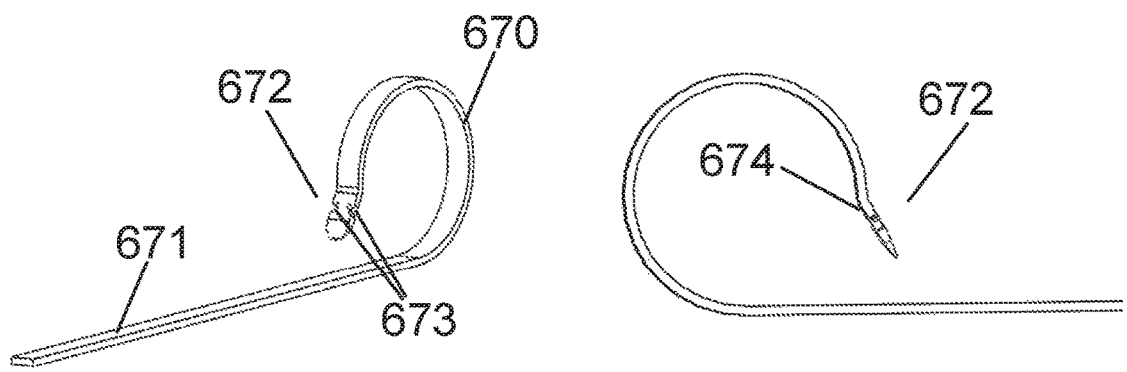
FIG. 56 is a perspective view of a shape memory element in accordance with the embodiments.
FIG. 57 is a side view of the shape memory element of FIG. 56.

Shown in FIG. 56 is an embodiment of a shape memory element. The primary loop 670 is generally circular and the flat section 671 may be attached to an actuation rod. The distal tip 672 is configured with two opposing slots 673 for the attachment of a passing element. The tip is rounded so as to not damage any unintended soft tissue structures as it encircles the bone.

Because the shape memory element is ideally of a diameter slightly smaller than the bone it encircles, there is a tendency, when the shape memory element has a constant radius at the loop, for to become stuck on the outer surface of the bone as the tip is advanced around the circular path. In other words, the tip will have a propensity to dig itself into the bone when trying to navigate its circumference. For this reason, the tip is ideally shaped to straighten or bend slightly outward as with a shepherd's hook. The profile view shown in FIG. 57 is of the same embodiment as that of FIG. 56. From this view it can be seen that the distal tip 672 of the shape memory element does not continue the same circular path as the rest of the loop. Instead, there is a slight bend 674 or straightening outward of the element at the tip. This straight section or outward bend prevents the tip from becoming stuck in the bone.

Figure 58:
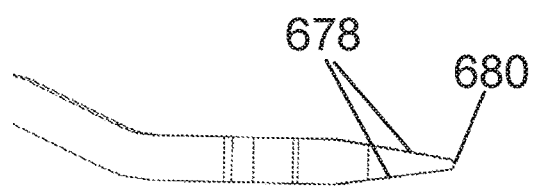
FIG. 58 is a profile view of the tip of the shape memory element of FIGS. 56 and 57 in accordance with the embodiments.

As mentioned previously, penetration through soft tissue surrounding the bone is necessary. Therefore the sides 678 of the distal tip are beveled in an embodiment as shown in FIG. 58. In embodiments, the beveled edges terminate in a small radius 680, while in other embodiments, the beveled edges continue to a sharp edge. Other embodiments may also include a pointed tip similar to a needle for better penetration of soft tissue.

Figures 59, 60:
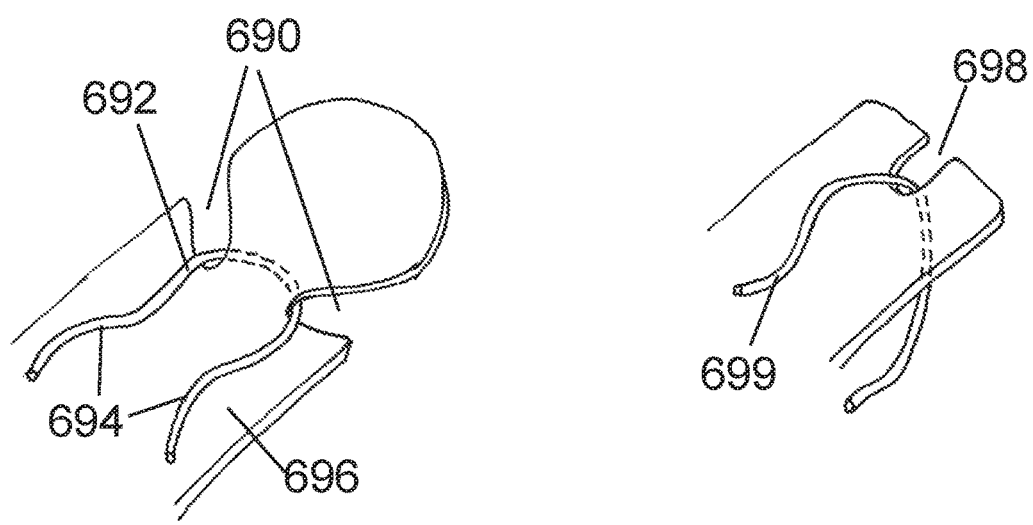
FIG. 59 is a perspective view of the tip of a shape memory element with a passing element installed in accordance with the embodiments.
FIG. 60 is a perspective view of another embodiment of a tip of a shape memory element with a passing element installed.
Figure 61:
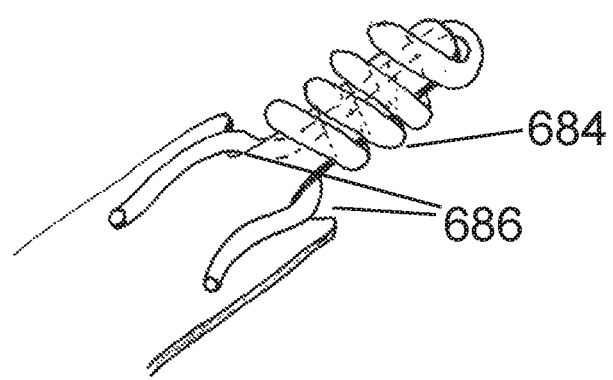
FIG. 61 is a perspective view of yet another embodiment of a tip of a shape memory element with a passing element installed.

As described earlier, the passing element is releasably attached to the distal tip of the shape memory element. FIGS. 59-61 show embodiments of passing element attachment configurations. FIG. 59 shows an embodiment of a distal tip/passing element configuration. The distal tip, as shown in previous embodiments, has two opposing angled slots 690 into which the passing element 692 rests as it is looped around the tip. The slots serve to hold the passing element in place after it is tensioned during loading. In embodiments the slots are straight across from each other, rather than angled. This configuration has the advantage of keeping both legs 694 of the passing element disposed on the back 696 of the shape memory element. This works in concert with the previously described passing element control feature in FIGS. 53-55 to keep the passing element aligned properly on the instrument as well as the shape memory element.

FIG. 60 is an embodiment of another distal tip/passing element configuration. In this simple configuration, a single notch 698 is disposed on the tip, through which the passing element 699 passes.

FIG. 61 is another embodiment of a distal tip/passing element configuration. In this embodiment a single post 682 is disposed at the tip of the shape memory element around which the passing element is wrapped. In embodiments, various configuration of wraps may be utilized. In the embodiment shown, after completing several wraps 684 around the post from the bottom upwards, the end is turned and fed back down under the existing loops similar to a fisherman's knot on a hook. The embodiment shown also includes the use of opposing notches 686 to guide the passing element onto the back of the shape memory element.

The passing element in embodiments may be a flexible member such as a suture or wire. In the case of a wire embodiment, one braid of small diameter filaments may be preferable in that it may better retain its flexibility. The wire may be stainless steel or nitinol or other suitable biocompatible metal.

FIGS. 62-65 show embodiments of passing elements that are formed from various configurations of suture. In an embodiment of a passing element shown in FIG. 62, a single suture stand 700 is configured with a loop 702 on each end. The loops may be the same strand that is looped over and knotted or manufactured as a bifurcated braid. The primary function of the two loops is for passage (pulling) of a prosthetic band or tendon graft in either direction, after the suture strand 700 has been passed (see, for example, FIG. 44). Further, a passing suture may be used to pass multiple other passing sutures. All of the embodiments shown are appropriate to work with disclosed embodiments of shape memory elements and passing instruments.

Figure 62:
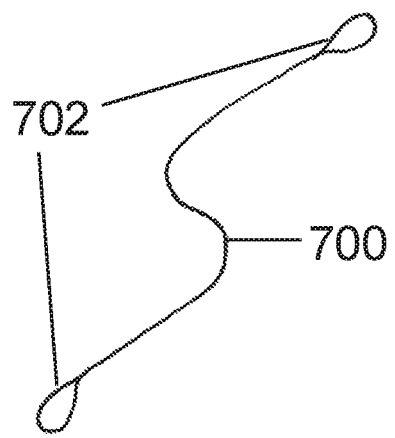
FIG. 62 is a perspective view of a passing element in accordance with the embodiments.
Figure 63:
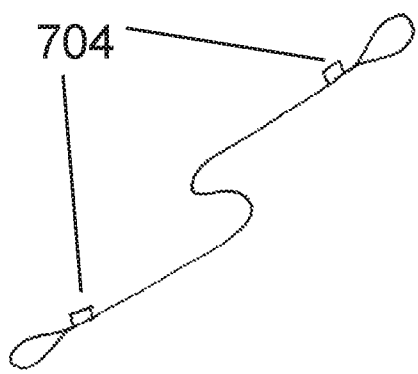
FIG. 63 is a perspective view of a another embodiment of a passing element.

The embodiment shown in FIG. 63 is similar to the double embodiment of FIG. 62 with the addition of tabs 704 on each end near the loops to provide something to grab with surgical instruments when using the passing instrument.

Figure 64:
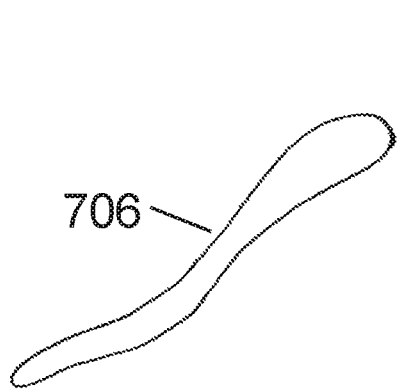
FIG. 64 is a perspective view of yet a another embodiment of a passing element.

The embodiment of FIG. 64 is a single continuous loop 706 of suture. The ends of the loop may be tied together in a knot or in embodiments may be braided or heat-staked together.

Figure 65:
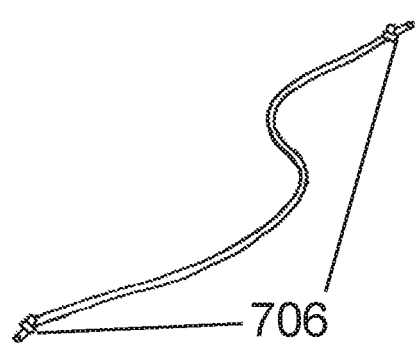
FIG. 65 is a perspective view of still yet another embodiment of a passing element.

The embodiment of FIG. 65 is a single suture strand with knots 708 in each end.

Figures 66, 67:
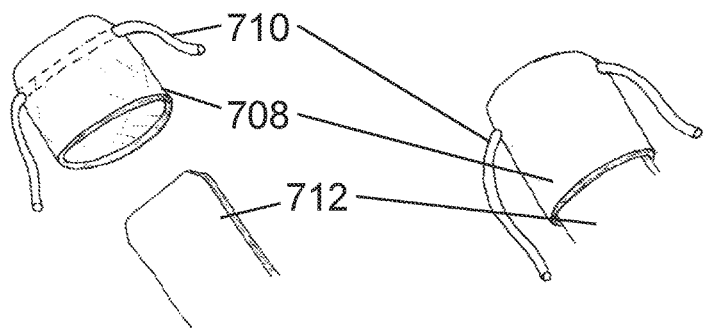
FIG. 66 is a perspective view of a passing cap with a passing element in accordance with embodiments.
FIG. 67 is a perspective view of another embodiment of a passing cap with a passing element.

FIGS. 66 and 67 show an embodiment of a passing cap 708. The passing cap facilitates connection of the passing element to the shape memory element. The passing cap 708 adds the advantage of providing a more substantial element that the user may grab when passing. Further, the cap 708 may be useful for passing instrument embodiments wherein it is desired to deliver the passing element back to the cannula. FIG. 66 shows a braided cap 708 preferably made of flexible material such as suture or small gage wire. A passing element 710 is shown passing completely through the cap from one side to the other. This is easily accomplished with a woven structure for the cap 708, which allows passage of needles, etc., through the fiber of the weave. FIG. 67 is a view of the passing cap 708 with passing element 710 attached and mounted onto a shape memory element 712. In alternate embodiments, a passing cap may be constructed of solid flexible material such as rubber, silicone or molded thermoplastic.

In surgery, it may be beneficial for the shape memory element to deliver the passing element construct all the way around the bone and reattach it to the cannula or a passing element-receiving feature thereon. Once the passing element has circumvented the bone and is reattached to the cannula, the cannula may be retrieved with both ends of the passing element intact, thus saving the surgeon time and effort. Thus, the passing element receiving feature can provide a passing element through a single opening in a patient. Embodiments below discuss a suture-receiving feature, where the passing element is a suture, but alternate embodiments can be utilized with any type of passing element.

Figures 68, 69:
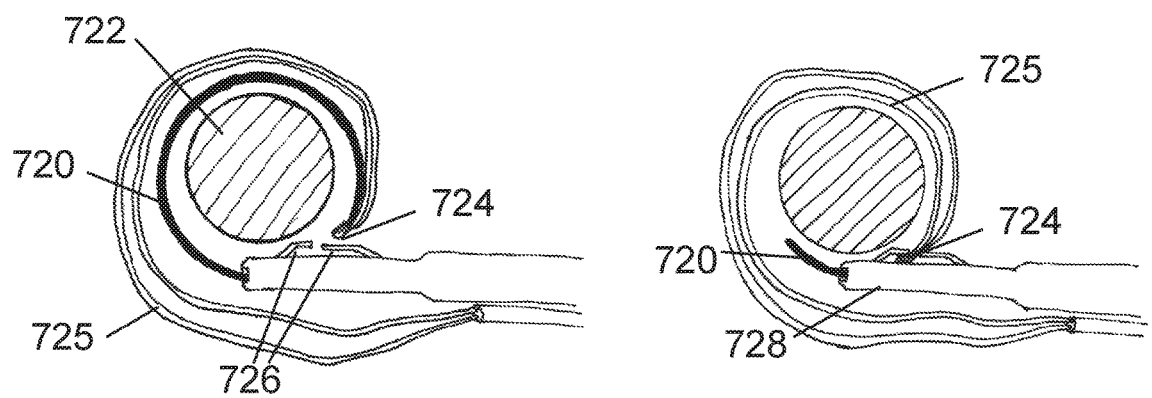
FIG. 68 is a schematic illustration of a passing instrument with a suture-receiving feature in place around a bone in accordance with embodiments.
FIG. 69 is a schematic illustration, in furtherance to FIG. 68, of the passing instrument with the suture-receiving feature, with a passing element attached to the suture-receiving feature.

FIG. 68 is an embodiment of a suture-receiving feature on the distal end of the cannula of the passing instrument. A shape memory element 720 is shown encircling a bone 722. The distal tip of the shape memory element is configured with a passing cap 724 of the type of embodiments 66-67 with a passing element 725 in tow. When the shape memory element has incrementally encircled the bone and reaches the cannula, it passes through two opposing cantilever elements 726. The tips of the elements 726 are spaced such that they have to deflect to allow passage of the passing cap. Upon retraction of the shape memory element 720 back into the cannula 728 as shown in FIG. 69, the passing cap 724 and associated passing element 725 are trapped on the outer surface of the cannula. Now both ends of the passing element may be retrieved simultaneously from the same direction by retracting the cannula.

Figures 70, 71:
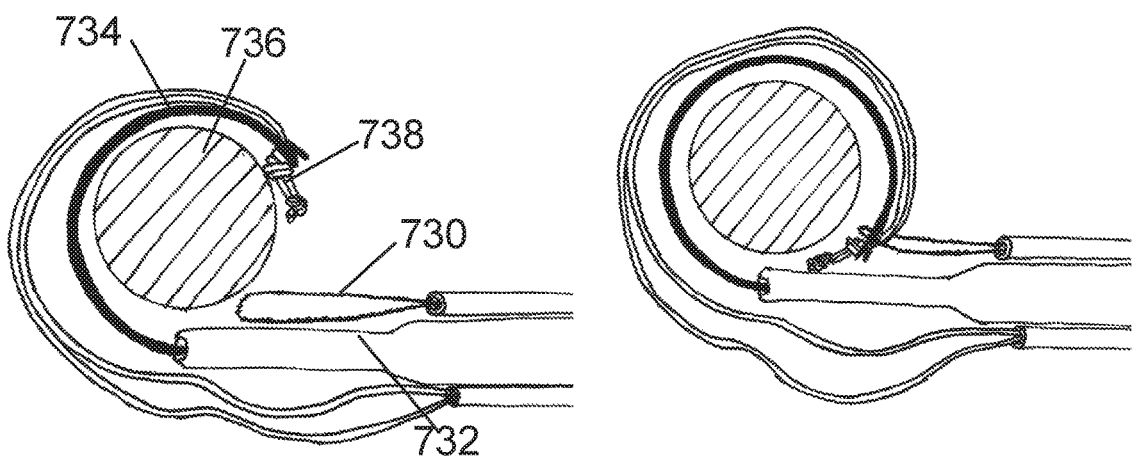
FIG. 70 is a schematic illustration of another embodiment of a passing instrument with a suture-receiving feature in place around a bone.
FIG. 71 is a schematic illustration of a passing instrument with a suture-receiving feature of FIG. 70, with a passing element attached to the suture-receiving feature.

FIG. 70 is another embodiment of a suture-receiving feature on the distal end of the cannula of a passing instrument. This embodiment has a wire or suture snare 730 retractably mounted on the cannula 732 and positioned so as to receive the shape memory element 734 as it incrementally encircles the bone 736. The shape memory element carries at its tip a passing element similar to that of embodiment of FIG. 65 with knots in the end of a suture 738. As the knots 738 pass into the snare 730, the snare may be retracted to capture and pull the passing element from the shape memory element as show in FIG. 71.

Figure 72:
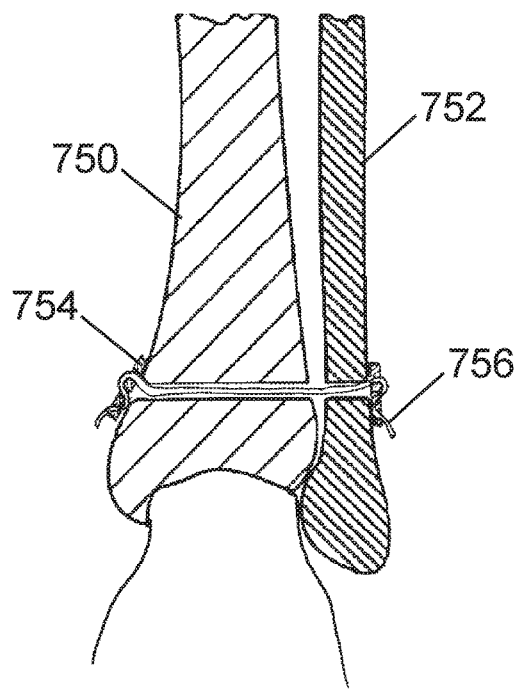
FIG. 72 is a section view of an embodiment of a prosthetic band system in place near the tibiofibular junction in accordance with the embodiments.

FIG. 72 shows an embodiment of the prosthetic band and a connector used in an ankle syndesmosis repair. The syndesmosis is where the tibia and fibula bones meet near the ankle. When the ligaments supporting this joint are damaged, the bones tend to separate and require support for healing. In FIG. 72, a prosthetic band of similar configuration as disclosed previously herein is stretched through a transverse hole though the two bones. Buckle-type connectors of similar configuration as disclosed previously herein are used to tension and anchor the bones at each end of the hole. Alternatively, a passing instrument as disclosed herein may be used to circumnavigate the bones and place a passing element around the bones which is then used to pull a prosthetic band into place around the bones where it may be tensioned and anchored with a connector of any of the embodiments disclosed herein.

Figure 73:
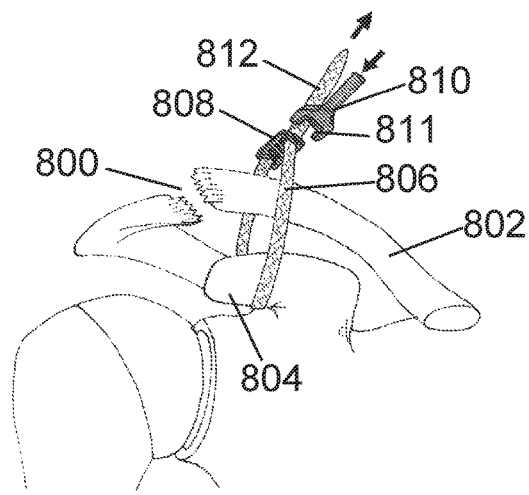
FIG. 73 is a schematic illustration of a prosthetic band with connector in place around the coracoid and clavicle of a shoulder with an AC joint dislocation and a counter traction tool being aligned.

Turning now back to prosthetic band systems for stabilizing the AC joint, FIG. 73 shows a shoulder with an AC joint separation 800, wherein the clavicle bone 802 is displaced superiorly with respect to the coracoid bone 804. A prosthetic band 806 with an integrated connector 808 as described in previous embodiments is shown looped under the coracoid and over the clavicle. The tip of the prosthetic band is show threaded though the receiving slot in the connector. In order to reduce the superiorly displaced clavicle, the prosthetic band must be tightened or cinched down over the clavicle. This can often be difficult, particularly in a minimally invasive surgical setting, due to the size of the connector and limited working space. In this instance, a counter traction tool 810 may be used to engage and stabilize the connector during the tightening or cinching process. The counter traction tool 810 may be disposed with a feature 811 that engages the connector to provide better stabilization of the connector. Such a feature may be in the form of a recess, groove, dimple, post, or other form that may provide mechanical engagement with the connector.

Figure 74:
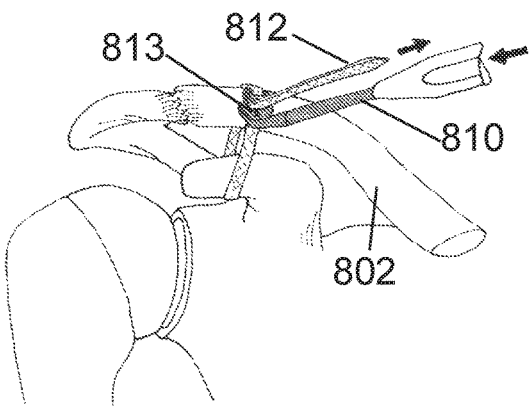
FIG. 74 is a schematic illustration, in furtherance to FIG. 73, of a counter traction tool in use to reduce the dislocation.

FIG. 74 shows the AC joint of FIG. 72 with the clavicle bone 802 in a reduced state by virtue of the tightened/cinched prosthetic band. The counter traction tool 810 is shown actively engaged with the connector, holding it stable against the clavicle bone. This allows the prosthetic band tip 812 to be pulled with significant force while maintaining the position of the connector against the clavicle. A locating feature 813 in the form of a hash mark is shown on the end of the counter traction tool which may correlate to a similar mark on the connector in order to provide the user with visible landmarks for orienting the counter traction tool with the connector. Said mark is ideally a laser mark but may also be pad printed or otherwise adorned on the tool and connector.

Figure 75:
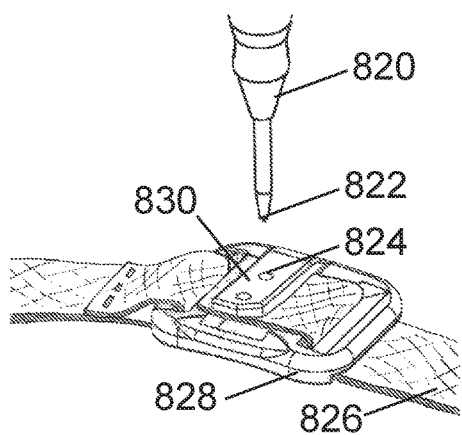
FIG. 75 is a schematic illustration of a punch being aligned to deflect the cleat of a prosthetic band connector.
Figure 76:
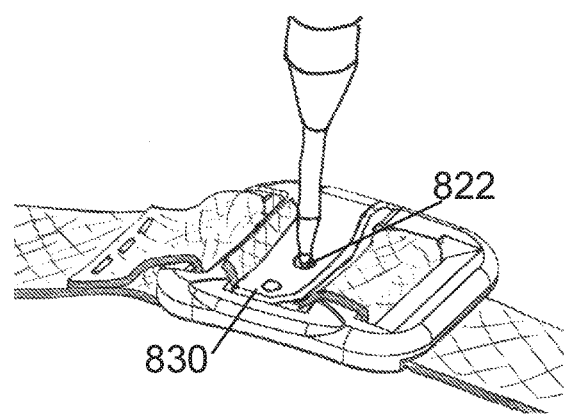
FIG. 76 is a schematic illustration, in furtherance to FIG. 75, of the punch tool having deflected the cleat of the prosthetic band connector.

Another adjunct tool that may facilitate the use of prosthetic band/connector system is the punch tool. In an embodiment, the punch tool is an automatic center punch as described earlier in this application, but may be simple punch requiring a mallet to deflect the cleat on the connector. Other tools may be used to deflect the cleat and lock the connector including but not limited to surgical graspers, pliers or needle drivers. FIG. 75 shows a prosthetic band 826 situated within the connector 828 and placed under the cleat 830 in the temporary locking mode. A punch tool 820 is shown with the punch tip 822 aligned to engage one of the dimples 824 on top of the cleat. FIG. 76 depicts a continuation of FIG. 75 wherein the punch tip 122 is fully engaged with the connector cleat 830 and has deflected it downward so as to effectively lock the prosthetic band within the connector.

Figure 77:
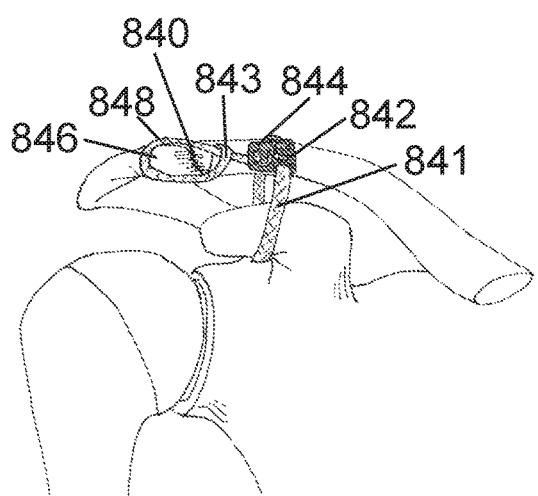
FIG. 77 is a schematic view of a prosthetic band and connector configured to span a acromioclavicular joint.

In the process of surgically repairing an AC joint separation, it may be beneficial to create stabilization across the actual acromioclavicular ligaments. This may be accomplished by spanning said joint by securing a prosthesis, suture, plate or the like to the clavicle and acromium bones, such as is shown in FIG. 77. A prosthetic band 841 is affixed around the clavicle and coracoid bones using a connector 842 as disclosed previously in this application. The connector 842 is disposed with an additional attachment point 844 which is configured to receive and affix a second prosthetic band 848 using methods previously described. In this embodiment, the prosthetic band 848 is configured with a prefabricated loop 843 allowing it to be attached to the acromium 846 in a luggage-tag type arrangement. Such an arrangement, with the prosthetic band spanning the acromioclavicular joint 840, may provide additional stabilization during healing.

Figure 78:
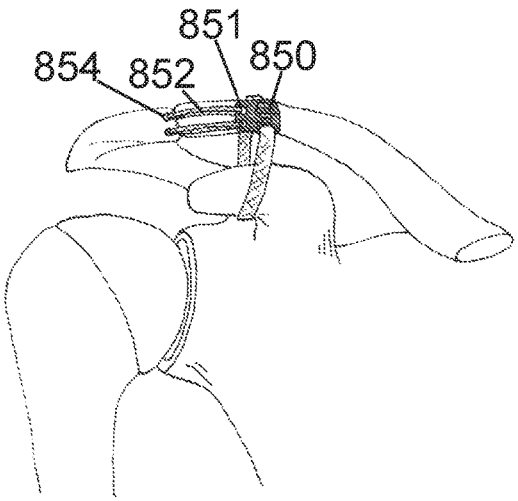
FIG. 78 is a schematic view of an embodiment of an AC joint repair system designed to span the acromioclavicular joint using suture.

FIG. 78 shows an additional embodiment of an AC joint-spanning repair. In this embodiment, the connector 850 is disposed with an additional attachment feature 851 which is configured to receive suture strands or cables. In this embodiment the feature 851 is in the form of holes or slots through the connector. The sutures or cables loop trough the attachment feature 851 holes/slots and span the AC joint where they are affixed to the acromium via bone tunnels 854. The bone tunnels 854 may be added during a procedure, for example, as described in earlier embodiments, by drilling holes in the bone. The suture or cable may pass through the bone tunnels 854 and terminate on the other side of the acromium using knots, pledgets, buttons or the like. Alternatively, the sutures or cables may pass through the bone tunnels 854 and span the joint again on the underside, ultimately returning and passing through bone tunnels (not shown) in the clavicle. In other embodiments the sutures may be anchored to the acromium using typical bone suture anchors rather than boring bone tunnels all the way through the bone.

As mentioned previously, many surgeons use tendon allograft as part of their AC joint repairs. In some cases, they may use only tendon allograft. The passing tool described earlier in this application may be used to help pass the tendon allografts around the coracoid and clavicle bones, however, the tendon would typically then be tied in knots over the clavicle and bolstered with suture stitches to prevent knot loosening. This process is tedious and results in a very large, undesirable tendon knot stack due to thick nature of the tendon. FIGS. 79-82 describe techniques and embodiments of devices to facilitate affixing of the tendon graft around the bones in an AC joint repair procedure.

Figure 79:
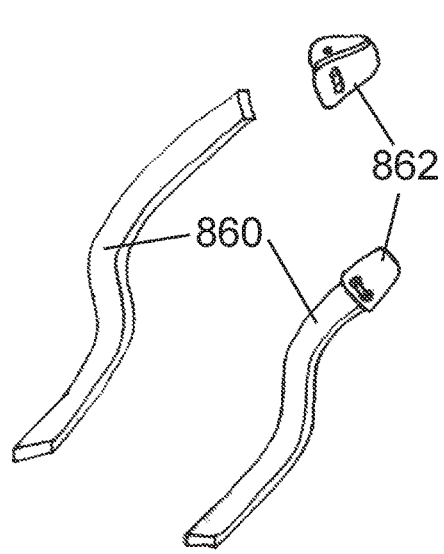
FIG. 79 is a schematic view of a tendon graft with a tip attachment.

FIG. 79 shows a tendon allograft 860 that may be looped around the coracoid and clavicle bones in a similar fashion to the prosthetic bands described herein. Because the typical tendon graft is quite flaccid, it may be challenging to thread into a connector for fixation. A tip 862 may be affixed to the tendon graft in order to allow easier interface with a connector. The tip 862 is generally flat in nature and may be composed of metal or plastic. In this embodiment, said tip is an elongated flat metallic tab that is crimped over the end of the tendon graft. The tip may be disposed with features designed to better grip the tendon graft, such as protrusions, spikes, roughened surfaces, etc. Alternatively, the tip may be applied with a lancing tool that deflects a small portion of the metal into the tendon graft, thus providing better retention. Many other tip attachment methods may be employed such as the use of staples, clips or sutures. The tip may be elongated such that the length is many times it's width to provide a longer effective stiff section for easier interface with a connector.

Figure 80:
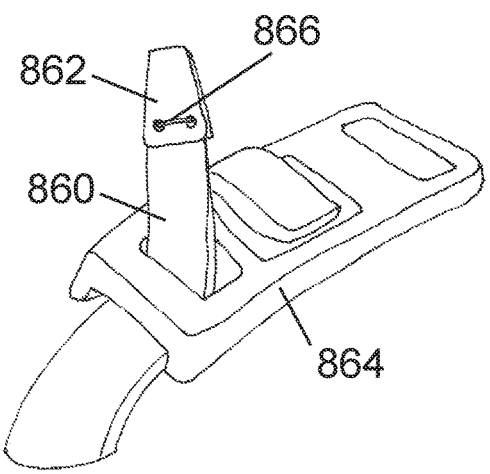
FIG. 80 is a schematic view of a tendon graft with a tip attachment inserted through a connector.

FIG. 80 shows the tendon allograft 860 with a tip attached using a suture strand 866 passed through holes in the tip. The tip 862 with attached allograft 860 is shown passed through the receiving slot of the connector 864. The connector 864 of this embodiment may be similarly configured as connectors described previously herein. However, the slots and openings on the connector through which the allograft passes may be of greater width to allow for passage of the thicker (by comparison to the prostheses described herein) tendon graft.

Figure 81:
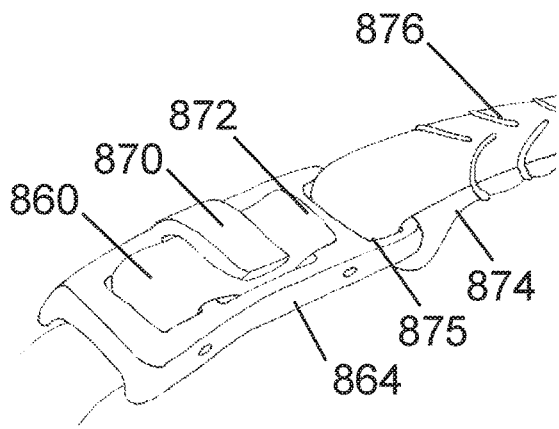
FIG. 81 is a schematic view of a tendon graft with connector showing tendon graft in temporary locked mode.

FIG. 81 is a continuation of FIG. 80 wherein a tendon graft 860 is shown affixed using a connector 864 configured to accept the graft. The tendon graft 860 has been placed under the cleat 870 on the connector 864 which, as described earlier, is a temporary or provisional locking mode, since it is still easy to adjust. The tip from FIG. 80 has been cut off or otherwise removed, leaving a free edge 872 of the tendon graft. The distal end 874 of the tendon graft 860 has been passed thought the opposite slot 875 of the of the connector, folded back onto itself and affixed using suture. This is the non-detachable end of the assembly which may be affixed prior to passing the tendon graft around the coracoid and clavicle bones (not shown).

Figure 82:
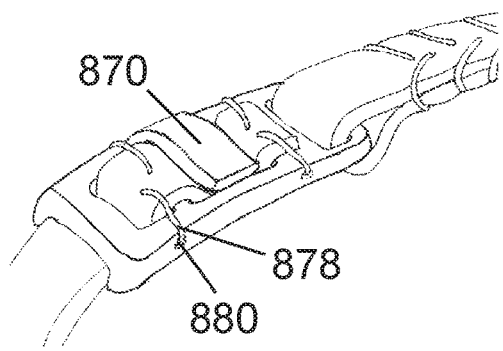
FIG. 82 is a schematic view of a tendon graft with connector showing tendon graft in permanent lock mode.

FIG. 82 shows the tendon graft/connector assembly of FIG. 81 in a permanently locked stated. The cleat 870 has been deflected, effectively locking the tendon graft in place. Additional tacking sutures 878 are shown in place to provide additional fixation if required. These sutures may be passed through small openings 880 in connector.

We turn now to other orthopedic applications and embodiments. The passing device described previously for circumventing bones in the shoulder is also useful for passing a suture around other bones or objects. The passing device can, for example, be used to circumvent other bones for other orthopedic procedures, specifically trauma applications. The femur bone in particular is subject to high loads and often fractures in a manner that requires repair. One common type of femur fracture, a periprosthetic fracture, occurs in patients with prior hip replacements. The stem of the prosthetic hip implant is imbedded deep into the femur bone and subsequent loading and anatomical conditions sometimes results in the femur bone fracturing or splintering around the prosthetic. In these cases, is becomes necessary to repair the fracture, often with circumferential cables which are sometimes combined with bone plates. The placement of the cables around the femur is technically demanding and the current passing tools are invasive and difficult to use. Embodiments of the passing tool described previously in this application have utility in this application.

Figure 83:
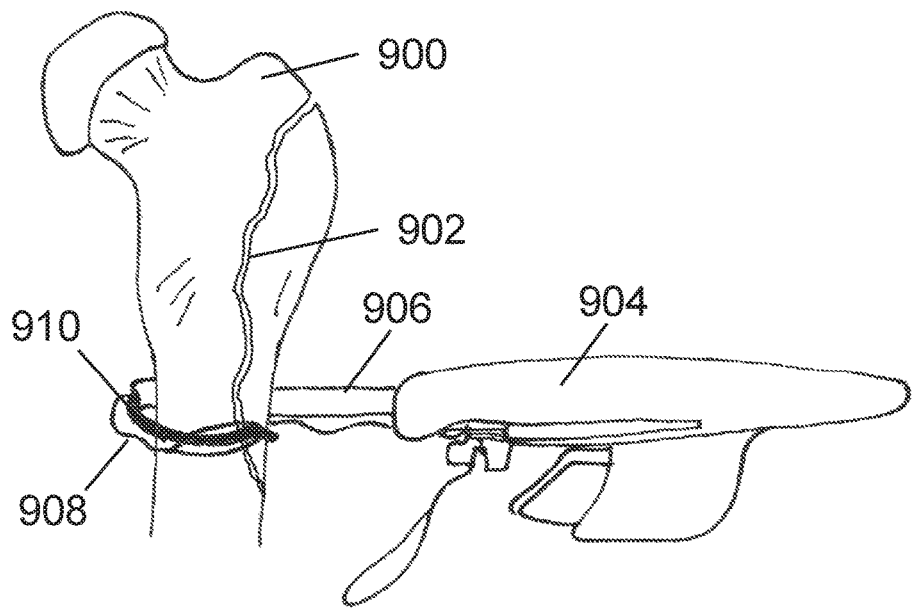
FIG. 83 is a schematic view of a passing device circumventing a femur bone.

FIG. 83 shows a femur bone 900 with a fracture 902. A passing device 904 of substantially the same design as disclosed previously herein is shown with the cannula 906 adjacent the femur bone. A passing element 908 is carried around the bone by the shape memory element 910 in the fashion described previously in this application. The passing element of this embodiment may differ from previously described embodiments in that it may not only be larger (the femur is a large bone) but also wider and thicker, resulting in a stiffer, stronger loop when deployed, yet remaining within the 8% strain limit as described previously.

FIG. 84 is a continuation of FIG. 83 wherein the passing element has been delivered around the bone, the shape memory element retracted, and the passing device removed from the field. The passing element 908 is shown with a free loop 904 on one end and a cerclage cable 904 attached to the other loop. A cerclage cable is a typically braided metal wire used in orthopedic trauma application. In other embodiments a cerclage cable may be attached directly to the end of the shape memory element for circumvention of the bone, thus not requiring the use of the passing element.

FIG. 85 is a continuation of FIG. 84 showing the cerclage cable 914 pulled completely around the bone by the passing element 908. Once the appropriate cables have been placed they are generally cinched to reduce the fracture and affixed with a crimp device or terminated at a bone plate.

FIGS. 86 and 87 show two different embodiments of attachment features for attaching a cerclage cable to a passing element. In the first embodiment shown in FIG. 86, the cerclage cable 916 is configured with a tip 918 which has a hole 920 in it. This hole allows the passing element to be attached to the cable in a luggage-tag configuration 922. Alternatively, the passing element could be passed through the hole and knotted, such that the knot cannot pass back through the hole. In the second embodiment shown in FIG. 87, the cable 924 is configured with a tip 926 that has button 928 or boss protruding from it. The passing element loop 930 may then be simply placed around the button. Alternatively, in embodiments, the passing element may be configured with connector elements which allow attachment of a cerclage cable. Said connecter element may take the form of a female connector which is design with an open distal end, the opening sized to accept the tip of a cerclage cable. The connector tapers to a smaller diameter back from the female opening to transition smoothly into the passing element. Such a taper allows smooth pull-through of the cerclage cable when being pulled around a bone and through soft tissue, lowering the required force and preventing snags. The female connector at the distal tip of the passing element may also be configured so as to securely retain the tip of the cerclage cable. This may be accomplished through a friction fit, utilizing polymers or rubbers with a high coefficient of friction. Alternatively, it may be accomplished with the use of a flexible, braided or woven tubular construct made from polymers typically used in suture products such as PET or UHMWPE. In such a braided female tubular connector, the retention of the cerclage cable is accomplished when the braided female connector is placed in tension, thus decreasing the diameter of the braid and effectively hugging the outer diameter of the cerclage cable which is placed inside the tubular structure. In other embodiments, the female connector for attaching the cerclage cable may be molded from polymers or rubbers and may have a variety of other positive engagement features which retain the cerclage cable within the female connector.

Figure 88:
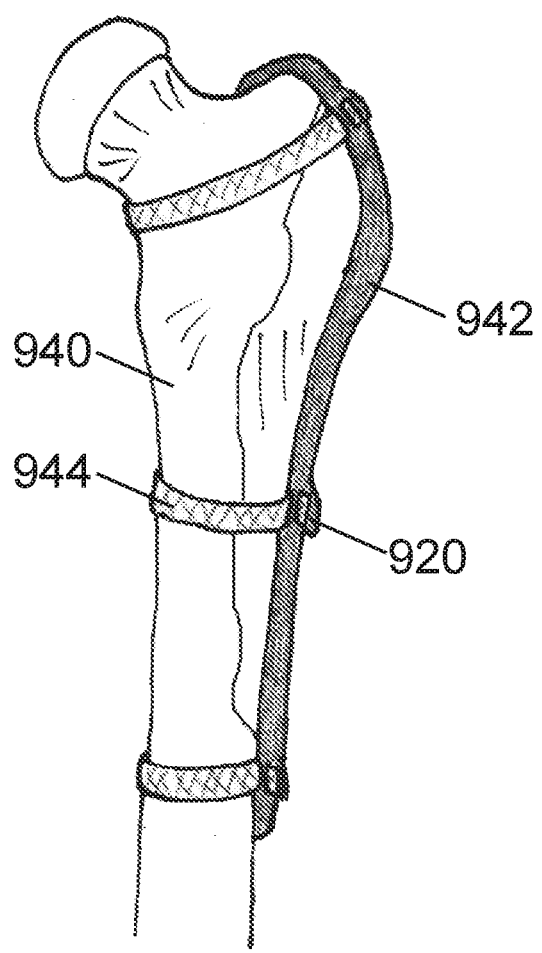
FIG. 88 is a perspective view of a fracture plate and prosthetic band system for repairing long bone fractures.

As described previously, cerclage cables may be passed with the aid of the device of the present invention and affixed to a bone plate to reduce a fracture. FIG. 88 shows an embodiment of a bone plate system which utilizes a prosthetic band as described previously herein. Shown is a fractured femur bone 940 with a bone plate 942 which is affixed with multiple prosthetic bands 944 of a design described earlier in this application. The prosthetic bands are affixed to the bone plate using a locking cleat mechanism as described in association with connectors and plates earlier in this application. The prosthetic bands are advantageous in that they are wider than cerclage cables, thus better distributing the load. Additionally, the inherently soft nature of the prosthetic band would eliminate sharp ends at the terminations points which can irritate surrounding soft tissue.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A system, comprising:
   a passing element;
   a shape memory passing device comprising a cannula and a shape memory element with an end configured to be detachably coupled with the passing element, the shape memory passing device being operable to extend the shape memory element from the cannula so that the shape memory element reconfigures from a constrained configuration to a curved deployed configuration; and
   a prosthetic device comprising an elongate band having a first end and a second ends, and a connector;
   wherein:
      the shape memory passing device is configurable to extend at least partially around a first bone of an animal with the passing element attached;
      the passing element is attachable to the prosthetic device to pull the elongate band of the prosthetic device into position around the first bone and a second bone of the animal; and
      the connector is operable to fixedly attach the elongate band in a tensioned state around the first bone and the second bone in a temporary fixation and in an adjusted permanent fixation so as to set the separation of the first bone and the second bone.

2. The system of claim 1, wherein the elongate band of the prosthetic device comprises:
   means for temporarily affixing the second end to the connector while the band is in a tensioned state around two bones, the means for temporarily fixing permitting adjustment of the tensioned state; and
   means for fixing the second end to the connector after the tensioned state has been adjusted.

3. The system of claim 2, wherein the means for temporarily fixing comprises a receiving slot for the elongate band of the prosthetic device that bends the band and provides resistance to movement of the elongate band relative to the connector.

4. The system of claim 2, wherein the means for temporarily fixing comprises a locking cleat for frictionally receiving the elongate band of the prosthetic device over a slot.

5. The system of claim 4, wherein the means for temporarily fixing comprises deflection of the locking cleat.

6. The system of claim 1, wherein the connector comprises a bone plate for stabilizing at least one of the bones when the prosthetic device is installed.

7. The system of claim 1, wherein the first bone is a coracoid, and the second bone is a clavicle.

8. The system of claim 1, wherein the first bone is a tibia, and the second bone is a fibula.

9. The system of claim 1, wherein the prosthetic device is fixedly attached in a tensioned state over the second bone.

10. The system of claim 1, wherein friction holds the elongate band in the tensioned state, the friction sufficient to keep the first bone and the second bone in a reduced position and simultaneously allow movement of the elongate band from the temporary fixation to the adjusted permanent fixation.

11. The system of claim 10, wherein the movement includes loosening or tightening the elongate band.

12. The system of claim 1, wherein the tensioned state holds a force at least equivalent to the force required to reduce the two bones; and
wherein the force after the tensioned state has been adjusted is at least equivalent to or greater than a strength of augmented native ligaments.

13. The system of claim 12, wherein the force in the temporary fixation is between about 10N and 100N and the force in the adjusted permanent fixation is between about 450N and 750N.

14. The system of claim 1, wherein the shape memory element has a flat cross-sectional shape having a thickness in a range from 0.015 inch to 0.06 inch and a width in a range from 0.05 inch to 0.25 inch.

15. The system of claim 14, wherein the shape memory element has a centerline curvature in a range from 0.3 inch to 1.0 inch in the curved deployed configuration.

16. The system of claim 1, wherein the passing element is disposed outside of the cannula.

17. A system, comprising:
a passing element;
a shape memory passing device having comprising a cannula and a shape memory element with an end configured to be detachably coupled with the passing element, the shape memory passing device being operable to extend the shape memory element from the cannula so that the shape memory element reconfigures from a constrained configuration to a curved deployed configuration; and
a prosthetic device comprising an elongate band having a first end and a second ends, and a connector;
wherein:
the shape memory passing device is configurable to extend at least partially around a first bone of an animal with the passing element attached;
the passing element is attachable to the prosthetic device to pull the elongate band of the prosthetic device into position around the first bone and a second bone of the animal; and
the connector is operable to fixedly attach the elongate band in a tensioned state around the first bone and the second bone in a temporary fixation and in an adjusted permanent fixation so as to set the separation of the first bone and the second bone; wherein the elongate band of the prosthetic device comprises:
a means for temporarily affixing the second end to the connector while the band is in a tensioned state around two bones, the means for temporarily fixing permitting adjustment of the tensioned state; and
a means for fixing the second end to the connector after the tensioned state has been adjusted.

* * * * *